United States Patent
Sasaki et al.

(10) Patent No.: US 11,602,494 B2
(45) Date of Patent: *Mar. 14, 2023

(54) COMPOSITIONS CONTAINING MICROCAPSULES COATED WITH DEPOSITION PROTEINS

(71) Applicant: INTERNATIONAL FLAVORS & FRAGRANCES INC., Union Beach, NJ (US)

(72) Inventors: Takashi Sasaki, Union Beach, NJ (US); Johan G. L. Pluyter, Union Beach, NJ (US)

(73) Assignee: INTERNATIONAL FLAVORS & FRAGRANCES INC., New York, NY (US)

(*) Notice: Subject to any disclaimer, the term of this patent is extended or adjusted under 35 U.S.C. 154(b) by 11 days.

This patent is subject to a terminal disclaimer.

(21) Appl. No.: 17/459,348

(22) Filed: Aug. 27, 2021

(65) Prior Publication Data
US 2022/0008299 A1    Jan. 13, 2022

Related U.S. Application Data

(63) Continuation of application No. 16/881,820, filed on May 22, 2020, now Pat. No. 11,129,778, which is a continuation of application No. 15/971,241, filed on May 4, 2018, now Pat. No. 10,695,272, which is a continuation of application No. 15/381,145, filed on Dec. 16, 2016, now Pat. No. 9,974,720.

(60) Provisional application No. 62/272,743, filed on Dec. 30, 2015.

(51) Int. Cl.
| | |
|---|---|
| A61K 8/11 | (2006.01) |
| A61K 8/84 | (2006.01) |
| A61Q 5/02 | (2006.01) |
| A61K 8/81 | (2006.01) |
| A61K 8/64 | (2006.01) |
| C11D 17/00 | (2006.01) |
| C11D 3/50 | (2006.01) |
| C11D 3/38 | (2006.01) |
| A61Q 13/00 | (2006.01) |
| C11D 3/37 | (2006.01) |

(52) U.S. Cl.
CPC ............ *A61K 8/11* (2013.01); *A61K 8/645* (2013.01); *A61K 8/8152* (2013.01); *A61K 8/84* (2013.01); *A61Q 5/02* (2013.01); *A61Q 13/00* (2013.01); *C11D 3/3726* (2013.01); *C11D 3/38* (2013.01); *C11D 3/505* (2013.01); *C11D 17/0039* (2013.01)

(58) Field of Classification Search
None
See application file for complete search history.

(56) References Cited

U.S. PATENT DOCUMENTS

| | | |
|---|---|---|
| 4,946,624 A | 8/1990 | Michael |
| 6,045,835 A | 4/2000 | Soper et al. |
| 6,979,467 B1 | 12/2005 | Garces Garces et al. |
| 9,974,720 B2 | 5/2018 | Sasaki et al. |
| 10,188,593 B2 | 1/2019 | Dihora et al. |
| 2006/0248665 A1 | 11/2006 | Pluyter et al. |
| 2009/0176291 A1 | 7/2009 | Boutique et al. |
| 2014/0023688 A1* | 1/2014 | Budijono ............... A61K 47/14 426/98 |
| 2015/0164117 A1 | 6/2015 | Kaplan et al. |
| 2015/0250689 A1 | 9/2015 | Dardelle et al. |
| 2018/0078468 A1 | 3/2018 | Jerri et al. |

FOREIGN PATENT DOCUMENTS

| | | |
|---|---|---|
| EP | 2934464 B1 | 2/2018 |
| WO | 2008142637 A1 | 11/2008 |
| WO | 2009080401 A2 | 7/2009 |
| WO | 2011056904 A1 | 7/2009 |
| WO | 2012001604 A2 | 1/2012 |
| WO | 2015023961 A2 | 2/2015 |
| WO | 2016185171 A1 | 11/2016 |
| WO | 2016193435 A1 | 12/2016 |
| WO | 2017102812 A1 | 6/2017 |
| WO | 2018002214 A1 | 1/2018 |
| WO | 2018019894 A1 | 2/2018 |
| WO | 2018019896 A1 | 2/2018 |
| WO | 2018077578 A1 | 5/2018 |

OTHER PUBLICATIONS

Voluminis Product Information Sheet, Sep. 7, 2010.
Office Communication dated Jun. 29, 2017 from U.S. Appl. No. 15/381,145, filed Dec. 16, 2016.
Office Communication dated Apr. 26, 2019 from U.S. Appl. No. 15/971,241, filed May 5, 2018.
Office Communication dated Oct. 1, 2019 from U.S. Appl. No. 15/971,241, filed May 5, 2018.
Office Communication dated Jan. 21, 2021 from U.S. Appl. No. 16/881,820, filed May 22, 2020.
Nesterenko et al. (2013) "Vegetable proteins in microencapsulation: A review of recent interventions and their effectiveness," Industrial Crops and Products 42:469-479.
Nesterenko et al. (2014) "Comparative study of encapsulation of vitamins with native and modified soy protein," Food Hydrocolloids 38:172-179.

\* cited by examiner

*Primary Examiner* — Melissa S Mercier
(74) *Attorney, Agent, or Firm* — Licata & Tyrrell P.C.

(57) ABSTRACT

A microcapsule composition containing microcapsules is provided as is a method for making the microcapsule composition and using the microcapsule composition in consumer products.

5 Claims, No Drawings

COMPOSITIONS CONTAINING MICROCAPSULES COATED WITH DEPOSITION PROTEINS

CROSS-REFERENCE TO RELATED APPLICATION

This application claims priority to U.S. patent application Ser. No. 16/881,820 filed on May 22, 2020, which is a continuation of U.S. patent application Ser. No. 15/971,241 filed on May 4, 2018, now issued as U.S. Pat. No. 10,695,272, which is a continuation of U.S. patent application Ser. No. 15/381,145 filed on Dec. 16, 2016, now issued as U.S. Pat. No. 9,974,720, claiming the benefit of U.S. Provisional Application Ser. No. 62/272,743 filed on Dec. 30, 2015. The contents of all applications are incorporated herein by reference in their entireties.

BACKGROUND

Fragrance microcapsules are efficient delivery systems that can provide lasting release of fragrance in variety of applications. The challenge however is when the intended use of the product is to clean and rinse particles, oils and dirt, as is the case with shampoos, detergents, body wash and hair conditioners. Therefore, there is a need in the art for microcapsule compositions with improved deposition characteristics suitable for rinse-off consumer product applications.

WO 2008/142637 describes a coacervated capsule, wherein the core is composed of a hydrophobic material, and the shell is composed of a protein such as an albumin, vegetable globulin or gelatine, and optionally a non-protein polymer.

WO 2009/080401 discloses capsules composed of a shell and a carrier oil core, wherein the shell is permeable to free perfume and is composed of an aminoplast, protein, polyurethane, polysaccharide, gum or polymethylmethacrylate.

WO 2011/056904 provides an encapsulate containing a core, a shell having an inner and outer surface and a coating, wherein the coating is on the outer surface of the shell and is composed of a cationic polymer, e.g., a protein, and an anionic polymer, e.g., a protein.

WO 2012/001604 describes a coacervated capsule having a core composed of a mixture of a fatty component and a flavor or fragrance material encapsulated within a coating layer composed essentially of a protein, and optionally a non-protein polymer.

SUMMARY OF THE INVENTION

The present invention provides a microcapsule composition composed of a plurality of microcapsules each containing a polymeric wall and an active material encapsulated within the polymeric wall, wherein the polymeric wall is coated with a deposition protein. In some embodiments, the deposition protein is a cationically modified protein (e.g., a protein-acrylate copolymer comprising at least one nitrogen-containing acrylic moiety such as a tertiary or quaternary amine group), a protein-silanol copolymer, a protein-silane, a protein-siloxane copolymer, or a combination thereof. In certain embodiments, the deposition protein has the structure of Formula I or Formula II:

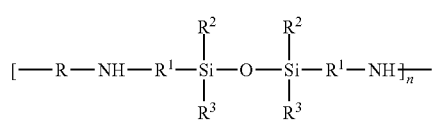

Formula I

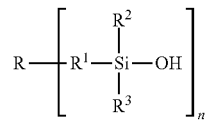

Formula II wherein R is a protein residue; $R^1$ is a protein cross-linker group; $R^2$ and $R^3$ are each independently hydrogen, hydroxyl, halo, $C_1$-$C_6$ alkyl, or $C_1$-$C_6$ alkoxy; and n is 1 to 100. Deposition proteins of the microcapsule composition can include a modified vegetable protein, wheat protein, marine collagen protein, keratin protein, silk protein, or milk protein, wherein the deposition protein has a molecular-weight in the range of 1000 to 500,000. In some embodiments, the active material of the microcapsule composition can include a fragrance, pro-fragrance, flavor, malodor counteractive agent, anti-inflammatory agent, anesthetic, analgesic, anti-viral agent, anti-infectious agent, anti-acne agent, skin lightening agent, insect repellant, emollient, skin moisturizing agent, vitamin or derivative thereof, nanometer to micron size inorganic solid, polymeric or elastomeric particle, or combination thereof. In other embodiments, the polymeric wall is composed of polyacrylate, polyurea, polyurethane, polyacrylamide, poly(acrylate-co-acrylamide), starch, silica, gelatin and gum Arabic, poly(melamine-formaldehyde), poly(urea-formaldehyde), or a combination thereof. In further embodiments, the microcapsule composition includes a second deposition aid.

A method for preparing the microcapsule composition of the invention is also provided. The method involves the steps of (a) providing a microcapsule slurry having a plurality of microcapsules each containing a polymeric wall and an active material encapsulated within the polymeric wall; and (b) curing the microcapsules and coating each of the microcapsules with a deposition protein. In some embodiments, the microcapsules are coated with the deposition protein at a temperature between 0 to 250° C. before, during or after curing the microcapsules. In other embodiments, the microcapsules are coated with a second deposition aid. In embodiments where the deposition protein is a protein-silanol copolymer, a protein-silane copolymer, a protein-siloxane copolymer, or a combination thereof, the microcapsules are coated at a temperature between 35 to 75° C. before, during or after curing the microcapsules. In some embodiments, the deposition protein is cross-linked with a cross-linking agent, e.g., a transglutaminase or alkoxysilane.

A consumer product containing the microcapsule composition is also provided, wherein said consumer product can include one or more different microcapsules, free active material, or a combination thereof. Consumer products include, but are not limited to a shampoo, hair conditioner, body wash, detergent, softener, bar soap, scent booster, or hard surface cleaner.

DETAILED DESCRIPTION OF THE INVENTION

It has now been found that modified proteins serve as deposition performance enhancers for microcapsules in various rinse-off consumer product applications. Without wishing to be bound by theory, it is posited that proteins may potentially improve the interactions to various substrates such as hair and skin.

Accordingly, this invention provides a microcapsule composition composed of a plurality of microcapsules each containing a polymeric wall and an active material encapsulated within the polymeric wall, wherein the polymeric wall is coated with a deposition protein. The terms "capsule" and "microcapsule" are used interchangeably. Microcapsules of this invention preferably have a size in the range of from 0.01 to 1000 microns in diameter (e.g., 0.5 to 1000 microns, 1 to 200 microns, 0.5 to 150 microns, 0.1 to 100 microns, 2 to 50 microns, 5 to 25 microns, 2 to 15 microns, and 1 to 10 microns), wherein the capsule distribution can be narrow, broad, or multi-modal.

As with conventional deposition agents, a deposition protein of this invention aids in deposition of microcapsules to surfaces such as fabric, hair or skin. The protein component starting material which is used in the preparation of the deposition protein may be derived from either animal or vegetable sources, or by fermentation. Examples of proteins, which can be used as the protein component, include collagen, elastin, keratin, casein, or other milk protein; wheat protein; vegetable protein such as potato protein or soya protein; and/or silk protein. Wheat protein and/or potato protein are particularly preferred, and especially wheat protein.

The term "protein" is used herein to include both native (or chemically unmodified) and hydrolyzed proteins, and thus includes proteins as well as polypeptides, peptides, amino acids and/or peptones, the latter of which can be categorized as hydrolyzed proteins. Hydrolyzed proteins are preferred, particularly polypeptides and peptides, which may, for example, be produced by acid, alkali, and/or enzyme hydrolysis, of native proteins. In this respect, the molecular weight (average weight) of the protein component may vary over a wide range, such as for example in the range from 100 to 500,000 Daltons, e.g., preferably 30,000 to 200,000, more preferably 50,000 to 150,000, particularly 60,000 to 100,000, and especially 70,000 to 90,000 Daltons.

The composition of the amino acids in the protein component preferably includes at least 1%, preferably in the range from 2 to 25%, more preferably 3 to 15%, particularly 4 to 10%, and especially 6 to 8% w/w of basic amino acids. The basic amino acids will normally be arginine, lysine, and/or histidine.

Commercially available examples of proteins of use in preparing the deposition protein of this invention include, but are not limited to, COLLASOL (high molecular weight, soluble, marine collagen; Croda), CROPEPTIDE (hydrolyzed wheat protein and hydrolyzed wheat starch; Croda), CROSILK 10000 (hydrolyzed silk protein; Croda), CROTEIN (hydrolyzed collagen; Croda), HYDROLACTIN 2500 (hydrolyzed milk protein; Croda), HYDROSOLANUM (hydrolyzed vegetable protein; Croda), HYDROSOY 2000 PE (hydrolyzed soy protein; Croda), HYDROTRITICUM 2000 PE (hydrolyzed wheat protein; Croda), KERASOL (hydrolyzed keratin; Croda), PROLEVIUM (cottonseed protein hydrolyzate; Croda), PROSINA (hydrolyzed keratin; Croda), TRITISOL (Hydrolyzed wheat protein; Croda), Fision KeraVeg18 (wheat amino acids, soy amino acids; Tri-K), MILK-TEIN (hydrolyzed milk protein; Tri-K), Rice PRO-TEIN (hydrolyzed rice protein; Tri-K), RICE-QUAT C (cocodimonium hydroxypropyl hydrolyzed rice protein; Tri-K), SOY-QUAT L (laurdimonium hydroxypropyl hydrolyzed soy protein; Tri-K), WHEAT-QUAT C (cocodimonium hydroxypropyl hydrolyzed wheat protein; Tri-K), QUINOA PRO EX (hydrolyzed quinoa; Tri-K), BARLA-TEIN Pro (hydrolyzed barley protein; Tri-K), KERA-QUAT WKP (hydrolyzed keratin; Tri-K), KERA-TEIN 1000 (hydrolyzed keratin; Tri-K), KERA-TEIN 1000 SD (hydrolyzed keratin; Tri-K), Proto-lan 8 (cocoyl hydrolyzed collagen; Tri-K), Proto-lan KT (cocoyl hydrolyzed collagen; Tri-K), SILK AA-QUAT C (cocodimonium hydroxypropyl silk amino acids; Tri-K), AMINO SILK SF (silk amino acids; Tri-K), Collagen Hydrolyzate Cosmetic N-55 (Tri-K), FLAX-TEIN Pro (hydrolyzed linseed protein; Tri-K), SOY-TEIN NL (hydrolyzed soy protein; Tri-K), Silk PRO-TEIN (hydrolyzed silk; Tri-K), WHEAT-TEIN W (hydrolyzed wheat protein; Tri-K), and MARI-COLL N-30 (hydrolyzed collagen; Tri-K).

The deposition protein can be prepared by modifying native and/or hydrolyzed protein to include a cationic and/or silicon moiety. Accordingly, in certain embodiments, the deposition protein is a cationically modified protein, a protein-silanol copolymer, a protein-silane, a protein-siloxane copolymer, or a combination thereof.

Cationically Modified Deposition Protein. A cationically modified deposition protein includes quaternary ammonium protein derivatives as well as protein-acrylate copolymers having a nitrogen-containing acrylic moiety.

Quaternary ammonium protein derivatives can be prepared from protein hydrolyzates in a two-step reaction using chloracetyl chloride to form an acetyl linking agent on the protein and subsequent reaction with a fatty tertiary amine to form a quaternary ammonium salt of polypeptide. See, e.g., FR 1149161. A quaternary ammonium protein derivative can also be prepared using a 2-hydroxy-1,3-propylene linking group between the protein hydrolysate radical and the quaternerized amino group. See JP 7908688 and JP 7908728. Alternatively, a lipophilic tertiary amine can be reacted with an epihalohydrin in the presence of water and subsequently reacted with an aqueous hydrolyzed protein to form a cationic quaternary ammonium protein derivative. See, e.g., EP 0109074.

A protein-acrylate copolymer can be produced by reacting protein with one or more of acrylic monomers, preferably by free radical polymerization as known in the art. Alternatively, oligomeric- and/or polyacrylates may be reacted with the protein, for example by converting some of the amine groups in the polyacrylate into protected thiols using N-succinimidyl 3-(2-pyridyldithio)propionate (SPDP). Following deprotection, the thiolated acrylate polymer can be conjugated to the protein via disulphide or thioether linkages.

Protein-acrylate copolymers may be produced by reacting protein with quaternary acrylic monomers, oligomers and/or polymers, or alternatively quaternization can occur in situ, for example by reacting protein with tertiary amine acrylic monomers, oligomers and/or polymers and quaternizing in situ for example with diethyl sulphate (e.g., in aqueous solution), dimethyl sulphate (e.g., in DMF), or alkyl and aryl halides such as methyl chloride, methyl iodide, methyl bromide, ethyl chloride, and benzyl chloride. See, e.g., US 2013/0004450.

The acrylate component of the protein-acrylate copolymer may be formed from, or include the reaction product of, at least one nitrogen containing acrylic monomer. The monomer may include more than one nitrogen atom, but generally will include only one nitrogen atom. The nitrogen atom(s) is preferably part of an amine group. The amine group may be a primary, secondary, tertiary, and/or quaternary group. Preferably the amine group is a tertiary or quaternary, and particularly a quaternary amine group. Acrylic monomer, oligomer, and/or polymer may be reacted with the protein component in order to form the protein-acrylate copolymer. Quaternary acrylic monomer, oligomer, and/or polymer may be reacted with the protein component, or alternatively amine groups present in the copolymer may be quaternized in situ, i.e., after reaction of the protein component with the acrylate component.

The nitrogen containing acrylic monomer can be (meth) acrylamide, a mono-, di- or tri-($C_1$-$C_4$)alkylamino ($C_1$-$C_4$) alkyl(meth)acrylate, a mono-, di- or tri-($C_1$-$C_4$) alkylamino ($C_1$-$C_4$)alkyl(meth)acrylamide, and mixtures thereof. In certain embodiments, the acrylic monomer is a dialkylaminoalkyl (meth)acrylate, a quaternized dialkylaminoalkyl (meth)acrylate, an acid addition salt of a quaternized dialkylaminoalkyl (meth)acrylate, or mixtures thereof. More preferably, the acrylic monomer is N,N-dimethylamino ethyl methacrylate (DMAEMA), N,N-diethylamino ethyl acrylate, N,N-diethylamino ethyl methacrylate, N-t-butylamino ethyl acrylate, N-t-butylamino ethyl methacrylate, N,N-dimethylamino propyl acrylamide, N,N-dimethylamino propyl methacrylamide, N,N-diethylamino propyl acrylamide, N,N-diethylamino propyl methacrylamide, N,N,N-trimethylamino ethyl methacrylate (DMAEMA-MC), N,N,N-triethylamino ethyl acrylate, N,N,N-triethylamino ethyl methacrylate, N,N,N-trimethylamino propyl acrylamide, N,N,N-trimethylamino propyl methacrylamide, N,N,N-triethylamino propyl acrylamide, N,N,N-triethylamino propyl methacrylamide, or mixtures thereof.

Desirably at least 20, preferably at least 40, more preferably at least 60, particularly in the range from 80 to 100, and especially 90 to 100 mole % of the acrylic monomers include tertiary and/or quaternary, preferably quaternary, amine groups.

In addition to a nitrogen containing acrylic monomer, the acrylic component of the protein-acrylate copolymer can include one or more other acrylic monomers, e.g., acrylic acid and/or methacrylic acid, and/or esters thereof, especially an alkyl ester wherein the alkyl group contains up to 10, more preferably up to 6, carbon atoms. Suitable alkyl groups may be selected from methyl, ethyl, n-propyl, isopropyl, n-butyl, isobutyl, tertbutyl, hexyl, 2-ethyl, hexyl, heptyl, and n-octyl. In one embodiment, mixtures of any two or more of the aforementioned monomers are employed, for example an alkyl acrylate (such as ethyl acrylate and/or butyl acrylate) in combination with an alkyl methacrylate (such as methyl methacrylate).

The acrylate component may also include other, preferably optional, additional monomers, in addition to the aforementioned acrylic acid or methacrylic acid or esters thereof. Suitable additional monomers include, e.g., acrylonitrile, methacrylonitrile, halo-substituted acrylonitrile, halo-substituted methacrylonitrile, hydroxyethyl methacrylate, glycidyl acrylate, glycidyl methacrylate, itaconic acid, itaconic anhydride, and half esters of itaconic acid.

The protein-acrylate copolymer may be a random, graft, or block copolymer. The copolymer is preferably a graft or block copolymer, and more preferably a graft copolymer. The protein-acrylate copolymer may be represented schematically as follows:

protein chain-X-polyacrylate wherein X is a linking group resulting from the reaction of the protein with the (poly)acrylate, and the part derived from the protein is preferably NH or S, particularly NH, wherein the polyacrylate contains between 2 to 1000, 5 to 500, 10 to 200, or 20 to 100 acrylic monomers.

Commercially available examples of cationically modified deposition proteins include, but are not limited to, CROMOIST WQ (quaternized wheat protein; commercially available from Croda), CROQUAT WKP (quaternized hydrolyzed keratin; Croda), CROSILQUAT (silk protein hydrolyzate quaternized by ammonium chloride cocoyldimethylammonium; Croda), and Voluminis (ethyltrimonium chloride methacrylate/hydrolyzed wheat protein copolymer; Croda).

Protein-Silicon Copolymer Deposition Aid. Preferred protein-silicon copolymers are those wherein the copolymer is the reaction product of a protein hydrolyzate and an organofunctional silane. More preferably, the organofunctional silane includes an epoxysilane capable of reacting with one or more amino groups of the protein, such as glycidoxypropyltrimethoxysilane. Exemplary protein-silicon copolymers include protein-silanol (—Si—OH), protein-silane (—Si—H), protein-siloxane (—Si—OR), and combinations thereof.

The protein of the protein-silicon copolymer may be a native protein or a chemically modified protein (for example, quaternized) provided that some free amino groups are still present in the protein molecules. The organofunctional silane used for reaction with the protein component to form the copolymer must contain a functional group capable of reacting with the chain terminal and/or side chain amino groups of the protein. Suitable reactive groups include, for example, acyl halide, sulphonyl halide, anhydride, aldehyde and epoxide groups. The silicon component of the copolymer may be any compound which contains a siloxane group (Si—O—Si) or any silane capable of forming a siloxane in situ by condensation of silanol (Si—OH) groups (Scheme 1) or any alkoxysilane or halosilane which hydrolyses to form a corresponding silanol (Scheme 2) and then condenses to form a siloxane group (Scheme 1).

SCHEME 1

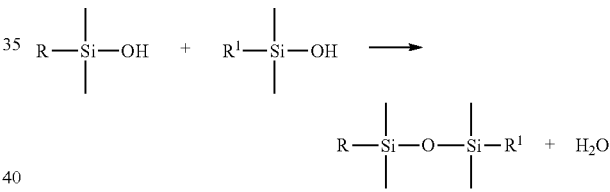

SCHEME 2

The silicone reactant is preferably capable of forming cross-links with the protein component. Cross-linking may be effected either through the use of polyfunctional silicone reactants or of monofunctional silicone reactants containing silanol groups (or alkoxysilane or halosilane groups convertible to silanol groups by hydrolysis) capable of forming siloxane cross-links by condensation between different chains. Such monofunctional silicone reactants should therefore have at least one and up to three hydroxy groups attached to at least one silicon atom in their structure.

A suitable method for the manufacture of copolymer compositions include heating the protein component and adjusting the pH to alkaline to deprotonate the amino groups. A calculated quantity of silane (based on the Formol titer, a technique described by Cobbett, et al. (1964) *J. Appl. Chem.* (London) 14:296-302) to estimate the degree of modification of amino groups in proteins) is then added, wherein the amount of silane is calculated to modify 5-40%, preferably 10-40% of the available amino groups. Following reaction, the pH is adjusted to acidic, and worked up in a conventional manner. See, e.g., U.S. Pat. No. 8,048,846.

Depending on the starting material, the protein-silicon copolymer used as a deposition protein of this invention has the structure of Formula I or Formula II:

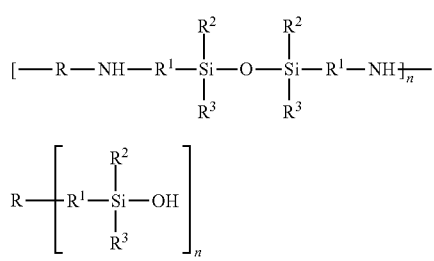

Formula I

Formula II wherein R is a residue of a protein; $R^1$ is a protein cross-linker group; $R^2$ and $R^3$ are each independently hydrogen, hydroxyl, halo, $C_1$-$C_6$ alkyl, or $C_1$-$C_6$ alkoxy; and n is 1 to 100.

"Halogen" or "halo" means fluorine, chlorine, bromine, or iodine.

"Alkyl" means a linear saturated monovalent hydrocarbon radical of one to six carbon (i.e., $C_1$-$C_6$) atoms, e.g., methyl, ethyl, propyl, 2-propyl, butyl (including all isomeric forms), or pentyl (including all isomeric forms), and the like.

"Alkoxy" means a radical —OR where R is alkyl as defined herein, e.g., methoxy, ethoxy, propoxy, or 2-propoxy, n-, iso-, or tert-butoxy, and the like.

Commercially available examples of protein-silanol copolymers, protein-silane copolymers, and protein-siloxane copolymers include, but are not limited to, CRODASONE W (hydrolyzed wheat protein PG-propyl silanetriol; Croda), CRODASONE P (hydrolyzed pea protein PG-propyl silanetriol; Croda), CRODASONE W (hydrolyzed wheat protein PG-propyl silanetriol; Croda), and KERAVIS (hydrolyzed vegetable protein PG-propyl silanetriol; Croda).

Core-Shell Encapsulation Systems. Encapsulation of active material such as fragrances is known in the art, see for example, U.S. Pat. Nos. 2,800,457, 3,870,542, 3,516,941, 3,415,758, 3,041,288, 5,112,688, 6,329,057, and 6,261,483. Wall forming polymers of use in this invention include polyurethane, polysiloxanes, polyurea, polyamide, polyimide, polyvinyl alcohol, polyanhydride, polyolefin, polysulfone, polysaccharide, protein, polylactide (PLA), polyglycolide (PGA), polyorthoester, polyphosphazene, silicone, lipid, modified cellulose, gums, polystyrene, and polyesters or combinations of these materials. Other polymeric wall materials that are functional are ethylene maleic anhydride copolymer, styrene maleic anhydride copolymer, ethylene vinyl acetate copolymer, and lactide glycolide copolymer. Biopolymers that are derived from alginate, chitosan, collagen, dextran, gelatin, gum Arabic, silk and starch can also be used as the encapsulating materials. Additionally, capsules can be made via the simple or complex coacervation of gelatin. Preferred encapsulating polymeric wall materials include those formed from urea-formaldehyde, melamine-formaldehyde phenolic-formaldehyde, urea-glutaraldehyde, melamine-glutaraldehyde, phenolic-glutaraldehyde, and combinations of these wall materials; polyurea (isocyanate-based), polyurethane, and combinations of these wall materials; acrylate-based hydrogels; polyurea/polyurethane-acrylic hybrid materials; polyamide and polyester-based materials; capsules produced using epoxy-based cross-linkers; silk fibroin microcapsules, and capsules based on silica and silica-derived materials which are typically produced using sol-gel processes.

Urea-Formaldehyde and Melamine-Formaldehyde Microcapsules. Urea-formaldehyde and melamine-formaldehyde pre-condensate capsule shell wall precursors are prepared by means of reacting urea or melamine with formaldehyde where the mole ratio of melamine or urea to formaldehyde is in the range of from about 10:1 to about 1:6, preferably from about 1:2 to about 1:5. For purposes of practicing this invention, the resulting material has a molecular weight in the range of from 156 to 3000. The resulting material may be used 'as-is' as a cross-linking agent for the aforementioned substituted or un-substituted acrylic acid polymer or copolymer or it may be further reacted with a $C_1$-$C_6$ alkanol, e.g., methanol, ethanol, 2-propanol, 3-propanol, 1-butanol, 1-pentanol or 1-hexanol, thereby forming a partial ether where the mole ratio of melamine/urea:formaldehyde:alkanol is in the range of 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. Nos. 3,516,846, 6,261,483, and Lee, et al. (2002) *J. Microencapsulation* 19:559-569.

Examples of urea-formaldehyde pre-condensates useful in the practice of this invention are URAC 180 and URAC 186, trademarks of Cytec Technology Corp. of Wilmington, Del. Examples of melamine-formaldehyde pre-condensates useful in the practice if this invention, include, but are not limited to, CYMEL U-60, CYMEL U-64 and CYMEL U-65, trademarks of Cytec Technology Corp. of Wilmington, Del. It is preferable to use, as the precondensate for cross-linking, the substituted or un-substituted acrylic acid polymer or co-polymer. In practicing this invention, the range of mole ratios of urea-formaldehyde precondensate/melamine-formaldehyde pre-condensate to substituted/un-substituted acrylic acid polymer/co-polymer is in the range of from about 9:1 to about 1:9, preferably from about 5:1 to about 1:5 and most preferably from about 2:1 to about 1:2.

In one embodiment of the invention, microcapsules with polymer(s) composed of primary and/or secondary amine reactive groups or mixtures thereof and cross-linkers can also be used. See US 2006/0248665. The amine polymers can possess primary and/or secondary amine functionalities and can be of either natural or synthetic origin. Amine-containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the LUPAMIN series of polyvinyl formamides available from BASF. The molecular weights of these materials can range from 10,000 to 1,000,000.

Urea-formaldehyde or melamine-formaldehyde capsules can also include formaldehyde scavengers, which are capable of binding free formaldehyde. When the capsules are for use in aqueous media, formaldehyde scavengers such as sodium sulfite, melamine, glycine, and carbohydrazine are suitable. When the capsules are aimed to be used in products having low pH, e.g., fabric care conditioners, formaldehyde scavengers are preferably selected from beta diketones, such as beta-ketoesters, or from 1,3-diols, such as propylene glycol. Preferred beta-ketoesters include alkyl-malonates, alkyl aceto acetates and polyvinyl alcohol aceto acetates.

Polyurea (Isocyanate-Based) and Polyurethane Microcapsules. Suitable polyurea or polyurethane microcapsules are prepared using one or more polyisocyanates and one or more cross-linker agents.

A polyisocyanate is a molecule having two or more isocyanate groups, i.e., O=C=N—, wherein said polyisocyanate can be aromatic, aliphatic, linear, branched, or cyclic. In certain embodiments, the polyisocyanate contains, on average, 2 to 4 —N=C=O groups. In particular embodiments, the polyisocyanate contains at least three isocyanate functional groups. In certain embodiments, the polyisocyanate is water-insoluble.

The polyisocyanate can be an aromatic or aliphatic polyisocyanate. Desirable aromatic polyisocyanates each have a phenyl, tolyl, xylyl, naphthyl or diphenyl moiety as the aromatic component. In certain embodiments, the aromatic polyisocyanate is a polymeric methylene diphenyl diisocyanate ("PMDI"), a polyisocyanurate of toluene diisocyanate, a trimethylol propane-adduct of toluene diisocyanate or a trimethylol propane-adduct of xylylene diisocyanate.

Suitable aliphatic polyisocyanates include trimers of hexamethylene diisocyanate, trimers of isophorone diisocyanate or biurets of hexamethylene diisocyanate. Additional examples include those commercially available, e.g., BAYHYDUR N304 and BAYHYDUR N305, which are aliphatic water-dispersible polyisocyanates based on hexamethylene diisocyanate; DESMODUR N3600, DESMODUR N3700, and DESMODUR N3900, which are low viscosity, polyfunctional aliphatic polyisocyanates based on hexamethylene diisocyanate; and DESMODUR 3600 and DESMODUR N100 which are aliphatic polyisocyanates based on hexamethylene diisocyanate, each of which is available from Bayer Corporation (Pittsburgh, Pa.).

Specific examples of wall monomer polyisocyanates include 1,5-naphthylene diisocyanate, 4,4'-diphenylmethane diisocyanate (MDI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, 3,3-bischloromethyl ether 4,4'-diphenyldiisocyanate. Sulfur-containing polyisocyanates are obtained, for example, by reacting 2 mol of hexamethylene diisocyanate with 1 mol of thiodiglycol or dihydroxydihexyl sulfide. Further suitable diisocyanates are trimethylhexamethylene diisocyanate, 1,4-diisocyanatobutane, 1,2-diisocyanatododecane and dimer fatty acid diisocyanate.

Other suitable commercially-available polyisocyanates include LUPRANATE M20 (PMDI, commercially available from BASF containing isocyanate group "NCO" 31.5 wt %), where the average n is 0.7; PAPI 27 (PMDI commercially available from Dow Chemical having an average molecular weight of 340 and containing NCO 31.4 wt %) where the average n is 0.7; MONDUR MR (PMDI containing NCO at 31 wt % or greater, commercially available from Bayer) where the average n is 0.8; MONDUR MR Light (PMDI containing NCO 31.8 wt %, commercially available from Bayer) where the average n is 0.8; MONDUR 489 (PMDI commercially available from Bayer containing NCO 30-31.4 wt %) where the average n is 1.0; poly[(phenylisocyanate)-co-formaldehyde] (Aldrich Chemical, Milwaukee, Wis.), other isocyanate monomers such as DESMODUR N3200 (poly(hexamethylene diisocyanate) commercially available from Bayer), and TAKENATE D110-N (xylene diisocyanate adduct polymer commercially available from Mitsui Chemicals corporation, Rye Brook, N.Y., containing NCO 11.5 wt %), DESMODUR L75 (a polyisocyanate base on toluene diisocyanate commercially available from Bayer), and DESMODUR IL (another polyisocyanate based on toluene diisocyanate commercially available from Bayer).

In some embodiments, the polyisocyanate used in the preparation of the microcapsules of this invention is a single polyisocyanate. In other embodiments the polyisocyanate is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is used to prepare the polyurea/polyureathane polymers as capsule wall materials.

The average molecular weight of certain suitable polyisocyanates varies from 250 to 1000 Da and preferable from 275 to 500 Da. In general, the range of the polyisocyanate concentration varies from 0.1% to 10%, preferably from 0.1% to 8%, more preferably from 0.2% to 5%, and even more preferably from 1.5% to 3.5%, all based on the weight of the capsule delivery system.

More examples of suitable polyisocyanates can be found in WO 2004/054362; WO 2015/023961; EP 0148149; EP 0017409 B1; U.S. Pat. Nos. 4,417,916, 4,124,526, 5,583,090, 6,566,306, 6,730,635, WO 1990/08468, WO 1992/13450, U.S. Pat. Nos. 4,681,806, 4,285,720 and 6,340,653.

Cross-linkers or cross-linking agents suitable for use with polyisocyanates each contain multiple (i.e., two or more) functional groups (e.g., —NH—, —NH$_2$ and —OH) that can react with polyisocyanates to form polyureas or polyurethanes. Examples include polyfunctional amines containing two or more amine groups (e.g., polyamines), polyfunctional alcohols containing two or more hydroxyl groups (e.g., polyols), epoxy cross-linkers, acrylate cross-linkers, and hybrid cross-linking agents containing one or more amine groups and one or more hydroxyl groups.

Amine groups in the cross-linking agents include —NH$_2$ and —R*NH, R* being substituted and unsubstituted $C_1$-$C_{20}$ alkyl, $C_1$-$C_{20}$ heteroalkyl, $C_1$-$C_{20}$ cycloalkyl, 3- to 8-membered heterocycloalkyl, aryl, and heteroaryl.

Two classes of such polyamines include polyalkylene polyamines having the following structures:

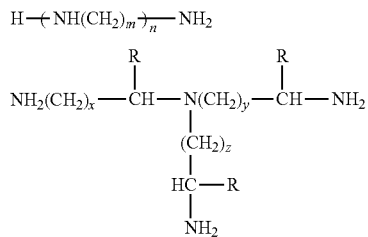

in which R is hydrogen or —CH$_3$; and m, n, x, y, and z each are independently integers from 0-2000 (e.g., 1, 2, 3, 4 or 5). Examples include ethylene diamine, 1,3-diaminepropane, diethylene triamine, triethylene tetramine, 1,4-diaminobutane, hexaethylene diamine, hexamethylene diamine, pentaethylenehexamine, and the like.

Another class of polyamines are polyalykylene polyamines of the type:

where R equals hydrogen or —CH$_3$, m is 1-5 and n is 1-5, e.g., diethylene triamine, triethylene tetraamine and the like. Exemplary amines of this type also include diethylenetriamine, bis(3-aminopropyl)amine, bis(hexanethylene)triamine.

Another class of amine that can be used in the invention is polyetheramines. They contain primary amino groups attached to the end of a polyether backbone. The polyether backbone is normally based on either propylene oxide (PO), ethylene oxide (EO), or mixed PO/EO. The ether amine can be monoamine, diamine, or triamine, based on this core structure. An example is:

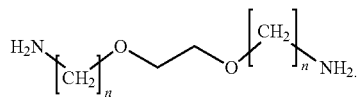

Exemplary polyetheramines include 2,2'-ethylenedioxy) bis (ethylamine) and 4,7,10-trioxa-1,13-tridecanediamine.

Other suitable amines include, but are not limited to, tris(2-aminoethyl)amine, triethylenetetramine, N,N'-bis(3-aminopropyl)-1,3-propanediamine, tetraethylene pentamine, 1,2-diaminopropane, N,N,N',N'-tetrakis(2-hydroxyethyl)ethylene diamine, N,N,N',N'-tetrakis(2-hydroxypropyl)ethylene diamine, branched polyethylenimine, 2,4-diamino-6-hydroxypyrimidine and 2,4,6-triaminopyrimidine.

Amphoteric amines, i.e., amines that can react as an acid as well as a base, are another class of amines of use in this invention. Examples of amphoteric amines include proteins and amino acids such as gelatin, L-lysine, D-lysine, L-arginine, D-arginine, L-lysine monohydrochloride, D-lysine monohydrochloride, L-arginine monohydrochloride, D-arginine monohydrochloride, L-ornithine monohydrochloride, D-ornithine monohydrochloride or a mixture thereof.

Guanidine amines and guanidine salts are yet another class of multi-functional amines of use in this invention. Exemplary guanidine amines and guanidine salts include, but are not limited to, 1,3-diaminoguanidine monohydrochloride, 1,1-dimethylbiguanide hydrochloride, guanidine carbonate and guanidine hydrochloride.

Commercially available examples of amines include JEFFAMINE EDR-148 having a structure shown above (where n=2), JEFFAMINE EDR-176 (where n=3) (from Huntsman). Other polyether amines include the JEFFAMINE ED Series, JEFFAMINE TRIAMINES, polyethylenimines from BASF (Ludwigshafen, Germany) under LUPASOL grades (e.g., LUPASOL FG, LUPASOL G20 waterfree, LUPASOL PR 8515, LUPASOL WF, LUPASOL FC, LUPASOL G20, LUPASOL G35, LUPASOL G100, LUPASOL G500, LUPASOL HF, LUPASOL PS, LUPASOL HEO 1, LUPASOL PN50, LUPASOL PN60, LUPASOL PO100 and LUPASOL SK). Other commercially available polyethylenimines include EPOMIN P-1000, EPOMIN P-1050, EPOMIN RP18W and EPOMIN PP-061 from NIPPON SHOKUBAI (New York, N.Y.). Polyvinylamines such as those sold by BASF under LUPAMINE grades can also be used. A wide range of polyetheramines may be selected by those skilled in the art. In certain embodiments, the cross-linking agent is hexamethylene diamine, polyetheramine or a mixture thereof.

The structures of specific cross-linking agents are shown in Table 1 below:

TABLE 1

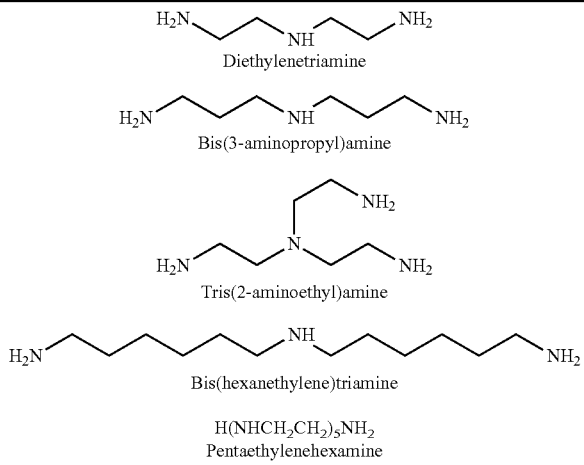

TABLE 1-continued
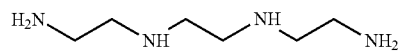
Triethylenetetramine
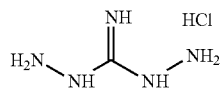
1,3-Diaminoguanidine monohydrochloride
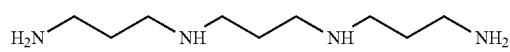
N,N'-Bis(3-aminopropyl)-1,3-propanediamine
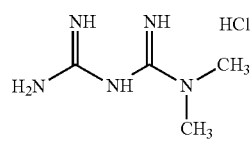
1,1-Dimethylbiguanide hydrochloride
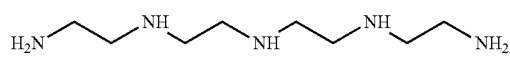
Tetraethylenepentamine
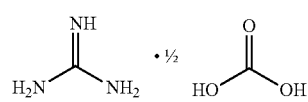
Guanidine carbonate
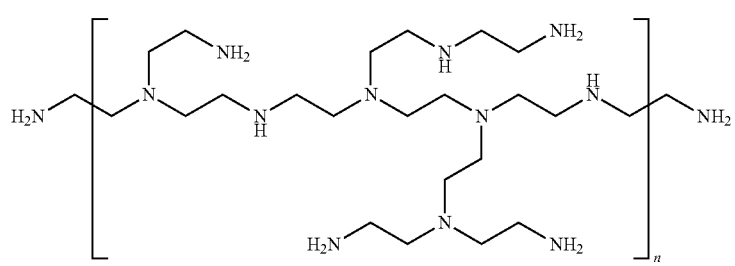
Branched Polyethylenimine
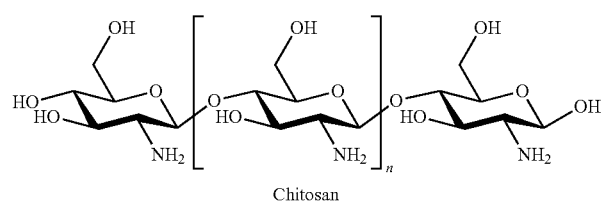
Chitosan TABLE 1-continued

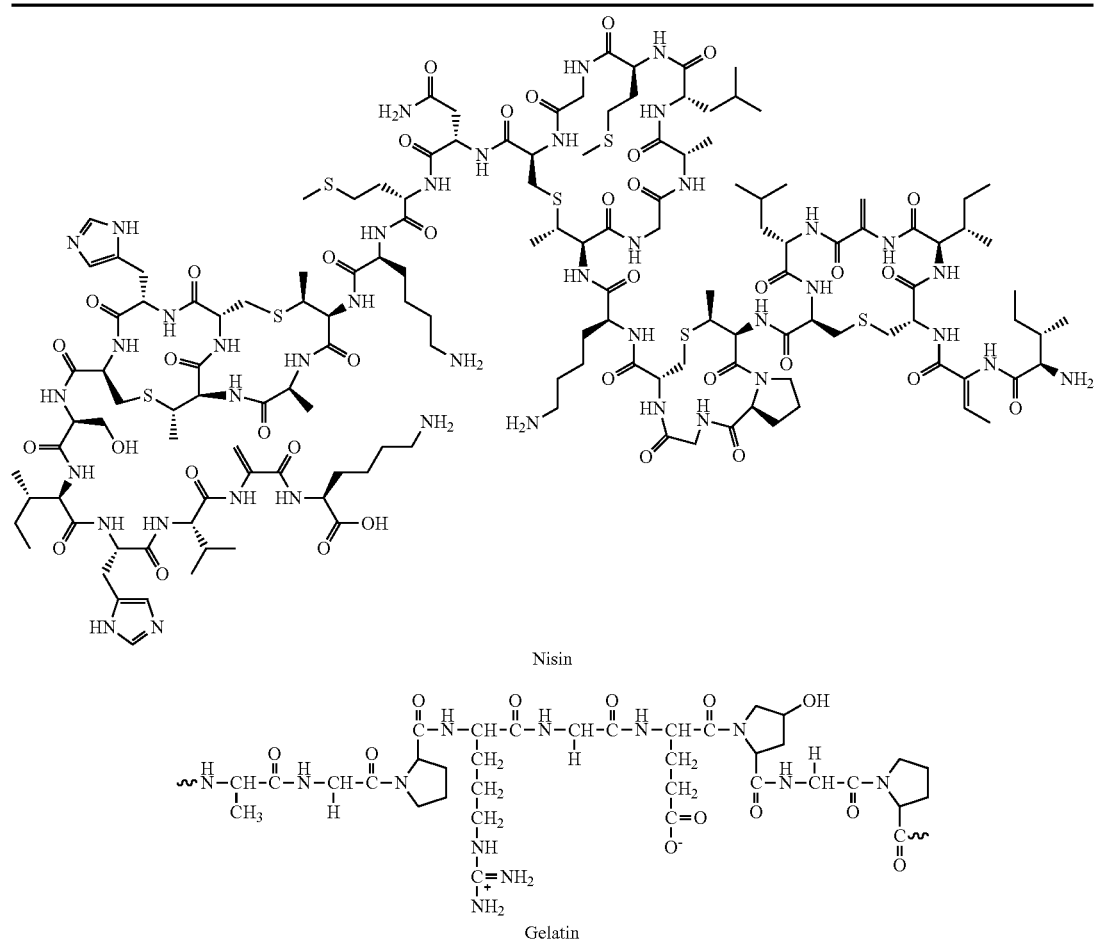

Nisin

Gelatin

Polyfunctional alcohols of use in this invention generally have at least two nucleophilic centers, e.g., ethylene glycol, hexylene glycol, pentaerythritol, glucose, sorbitol, and 2-aminoethanol.

The range of polyfunctional amines, polyfunctional alcohols, or hybrid cross-linking agents can vary from 0.1% to 5% (e.g., 0.2% to 3%, 0.2% to 2%, 0.5% to 2%, or 0.5% to 1%) by weight of the capsule delivery system. In one embodiment of the invention, the cross-linking agent is added to the capsule reaction at a temperature of 0-55° C. (e.g., 10-50° C., 15-45° C., 20-40° C., or 22-35° C.).

By adding an excess amount of a cross-linking agent, the polyurea/polyurethane formation is driven toward completion thereby reducing the amount of residual polyisocyanate. The reaction stoichiometry requires one amine/hydroxyl group per one isocyanate group. By way of illustration, when combining LUPRANATE M20 (having a molecular weight of 360 and isocyanate functionality of 2.7) and hexamethylenediamine (HMDA; having a molecular weight of 116.21 and amine functionality of 2), the stoichiometry of the system indicates that for each gram of HMDA, 2.23 grams of LUPRANATE is needed. The amount of amine will be in excess if more than one gram of HMDA is used per 2.23 grams of LUPRANATE M20. Using a cross-linker in excess, residual isocyanate amounts are reduced by at least 30%. After the capsules are formed, the free cross-link agent (e.g., hexamethylenediamine, amino-2-methyl-1-propanol, lysine, arginine, and histidine) can be present in the capsule slurry at a concentration of 20 ppm to 2%. The amounts of the residual isocyanate and free cross-linking agent can be removed by washing the capsule slurry with water or carbonate/bicarbonate solution (e.g., sodium carbonate, potassium carbonate, sodium bicarbonate, and potassium bicarbonate).

Catalysts of use in the preparation of microcapsules include metal carbonates, metal hydroxide, amino or organometallic compounds such as sodium carbonate, cesium carbonate, potassium carbonate, lithium hydroxide, 1,4-diazabicyclo[2.2.2]octane (i.e., DABCO), N,N-dimethylaminoethanol, N,N-dimethylcyclohexylamine, bis-(2-dimethyl-amino-ethyl) ether, N,N dimethylacetylamine, stannous octoate and dibutyltin dilaurate.

Polyacrylate/Polyacrylamide/Poly(acrylate-co-acrylamide) Microcapsules. Preferred polyacrylate precursor are bi- or polyfunctional vinyl monomers including by way of illustration and not limitation, allyl methacrylate/acrylamide, triethylene glycol dimethacrylate/acrylamide, ethylene glycol dimethacrylate/acrylamide, diethylene glycol dimethacrylate/acrylamide, triethylene glycol dimethacrylate/acrylamide, tetraethylene glycol dimethacrylate/acrylamide, propylene glycol dimethacrylate/acrylamide, glycerol dimethacrylate/acrylamide, neopentyl glycol dimethacrylate/acrylamide, 1,10-decanediol dimethacrylate/acrylimide, pentaerythritol trimethacrylate/acrylamide, pentaerythritol tetramethacrylate/acrylamide, dipentaerythritol hexamethacrylate/acrylamide, triallyl-formal trimethacrylate/acrylamide, trimethylol propane trimethacrylate/acrylamide, tributanediol dimethacrylate/acrylamide, aliphatic or aromatic urethane diacrylates/acrylamides, difunctional urethane acrylates/acrylamides, ethoxylated aliphatic difunctional urethane methacrylates/acrylamides, aliphatic or aromatic urethane dimethacrylates/acrylamides, epoxy acrylates/acrylamides, epoxymethacrylates/acrylamides, 1,3-butylene glycol diacrylate/acrylamide, 1,4-butanediol dimethacrylate/acrylamide, 1,4-butaneidiol diacrylate/acrylamide, diethylene glycol diacrylate/acrylamide, 1,6-hexanediol diacrylate/acrylamide, 1,6-hexanediol dimethacrylate/acrylamide, neopentyl glycol diacrylate/acrylamide, polyethylene glycol diacrylate/acrylamide, tetraethylene glycol diacrylate/acrylamide, triethylene glycol diacrylate/acrylamide, 1,3-butylene glycol dimethacrylate/acrylamide, tripropylene glycol diacrylate/acrylamide, ethoxylated bisphenol diacrylate/acrylamide, ethoxylated bisphenol dimethylacrylate/acrylamide, dipropylene glycol diacrylate/acrylamide, alkoxylated hexanediol diacrylate/acrylamide, alkoxylated cyclohexane dimethanol diacrylate/acrylamide, propoxylated neopentyl glycol diacrylate/acrylamide, trimethylol-propane triacrylate/acrylamide, pentaerythritol triacrylate/acrylamide, ethoxylated trimethylolpropane triacrylate/acrylamide, propoxylated trimethylolpropane triacrylate/acrylamide, propoxylated glyceryl triacrylate/acrylamide, ditrimethylolpropane tetraacrylate/acrylamide, dipentaerythritol pentaacrylate/acrylamide, ethoxylated penta-erythritol tetraacrylate/acrylamide, PEG 200 dimethacrylate/acrylamide, PEG 400 dimethacrylate/acrylamide, PEG 600 dimethacrylate/acrylamide, 3-acryloyloxy glycol monoacrylate/acrylamide, triacryl formal, triallyl isocyanate, and triallyl isocyanurate.

The monomer is polymerized in the presence of an activation agent (e.g., an initiator) at an elevated temperature (e.g., 30-90° C.) or under UV light. Exemplary initiators are 2,2'-azobis(isobutyronitrile) ("AIBN"), dicetyl peroxydicarbonate, di(4-tert-butylcyclohexyl) peroxydicarbonate, dioctanoyl peroxide, dibenzoyl peroxide, dilauroyl peroxide, didecanoyl peroxide, tert-butyl peracetate, tert-butyl perlaurate, tert-butyl perbenzoate, tert-butyl hydroperoxide, cumene hydroperoxide, cumene ethylperoxide, diisopropylhydroxy dicarboxylate, 2,2'-azobis(2,4-dimethylvaleronitrile), 1,1'-azobis-(cyclohexane-1-carbonitrile), dimethyl 2,2'-azobis-(2-methylpropionate), 2,2'-azobis[2-methyl-N-(2-hydroxyethyl)propionamide, sodium persulfate, benzoyl peroxide, and combinations thereof.

Emulsifiers used in the formation of polyacrylate/polyacrylamide/poly(acrylate-co-acrylamide) capsule walls are typically anionic emulsifiers including by way of illustration and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acryl-amido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates. The amount of anionic emulsifier is anywhere from about 0.1 to about 40 percent by weight of all constituents, more preferably from 0.5 to about 10 percent, more preferably 0.5 to 5 percent by weigh.

Polymeric stabilizers are often added to microcapsules containing polyacrylate, polyacrylamide, or poly(acrylate-co-acrylamide). Suitable stabilizers are cationic cellulose derivatives, quaternized gums, polyethylene imines, cationic polyacrylates, polyacrylamides, polyacrylates, gelatin, quaternized protein hydrolysates, quaternized amino silicones, hydroxyethyl cellulose, polyvinyl pyrrolidone, polyvinyl alcohol, styrene co-polymer with maleic anhydride or acrylic acid, and combinations thereof.

Silk Fibroin Microcapsules. Various methods of producing silk fibroin particles are known in the art. In some embodiments, the silk particles can be produced by a polyvinyl alcohol (PVA) phase separation method as described in, e.g., WO 2011/041395. Other methods for producing silk fibroin particles are described, for example, in US 2010/0028451 and WO 2008/118133 (using oil as a template for making silk microspheres or nanospheres), and in Wenk, et al. (2008) *J. Control. Release* 132:26-34 (using spraying method to produce silk microspheres or nanospheres).

In some embodiments, silk particles can be produced using a freeze-drying method as described in WO 2013/155404. Specifically, a silk fibroin foam can be produced by freeze-drying a silk solution. The foam then can be reduced to microcapsules. For example, a silk solution can be cooled to a temperature at which the liquid carrier transforms into a plurality of solid crystals or particles and removing at least some of the plurality of solid crystals or particles to leave a porous silk material (e.g., silk foam). After cooling, liquid carrier can be removed, at least partially, by sublimation, evaporation, and/or lyophilization. See also US 2015/0164117 and US 2015/0202304.

Silica-Based Capsules Produced with Sol-Gel Precursors. Suitable sol-gel precursors are compounds capable of forming gels such as compounds containing silicon, boron, aluminum, titanium, zinc, zirconium, and vanadium. Preferred precursors are organosilicon, organoboron, and organoaluminum including metal alkoxides and b-diketonates.

Suitable sol-gel precursors include in particular di-, tri- and/or tetrafunctional silicic acid, boric acid and alumoesters, more particularly alkoxysilanes (alkyl orthosilicates), and precursors thereof.

One example of sol-gel precursors suitable for the purposes of the invention are alkoxysilanes corresponding to the following general formula:

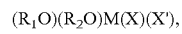

wherein X can be hydrogen or —OR$_3$; X' can be hydrogen or —OR$_4$; and R$_1$, R$_2$, R$_3$ and R$_4$ independently represent an organic group, more particularly a linear or branched alkyl group, preferably a $C_1$-$C_{12}$ alkyl. M can be Si, Ti, or Zr.

A preferred sol/gel precursor is alkoxysilanes corresponding to the following general formula: $(R_1O)(R_2O)Si(X)(X')$, wherein each of X, X', $R_1$, and $R_2$ is defined above.

Particularly preferred compounds are the silicic acid esters such as tetramethyl orthosilicate (TMOS) and tetraethyl orthosilicate (TEOS). A preferred compound includes Dynasylan® (organofunctional silanes commercially available from Degussa Corporation (Parsippany, N.J.)). Other sol-gel precursors suitable for the purposes of the invention are described, for example, in German Patent Application DE10021165. These sol-gel precursors are various hydrolyzable organosilanes such as, for example, alkylsilanes, alkoxysilanes, alkyl alkoxysilanes and organoalkoxysilanes. Besides the alkyl and alkoxy groups, other organic groups (for example, allyl groups, aminoalkyl groups, hydroxyalkyl groups, etc.) may be attached as substituents to the silicon.

Recognizing that metal and semi metal alkoxide monomers (and their partially hydrolyzed and condensed polymers) such as tetramethoxy silane (TMOS), tetraethoxy silane (TEOS), etc. are very good solvents for numerous molecules and active ingredients is highly advantageous since it facilitates dissolving the active materials at a high concentration and thus a high loading in the final capsules.

Additional polymer systems of use in the preparation of microcapsules include, e.g., aminoplast capsules and encapsulated particles as disclosed in GB 2006709 A; microcapsules having walls composed of styrene-maleic anhydride reacted with melamine-formaldehyde precondensates as disclosed in U.S. Pat. No. 4,396,670; an acrylic acid-acrylamide copolymer, cross-linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amido-aldehyde resin in situ polymerized capsules disclosed in EP 0158449 A1; etherified urea-formaldehyde polymer as disclosed in U.S. Pat. No. 5,204,185; melamine-formaldehyde microcapsules as described in U.S. Pat. No. 4,525,520; cross-linked oil-soluble melamine-formaldehyde precondensate as described in U.S. Pat. No. 5,011,634; capsule wall material formed from a complex of cationic and anionic melamine-formaldehyde precondensates that are then cross-linked as disclosed in U.S. Pat. No. 5,013,473; polymeric shells made from addition polymers such as condensation polymers, phenolic aldehydes, urea aldehydes or acrylic polymer as disclosed in U.S. Pat. No. 3,516,941; urea-formaldehyde capsules as disclosed in EP 0443428 A2; melamine-formaldehyde chemistry as disclosed in GB 2062570 A; and capsules composed of polymer or copolymer of styrene sulfonic acid in acid of salt form, and capsules cross-linked with melamine-formaldehyde as disclosed in U.S. Pat. No. 4,001,140.

Capsule Formation Aids. Most capsule formation aids are used as dispersants (namely, emulsifiers or surfactants). They facilitate the formation of stable emulsions containing nano- or micro-sized oil drops to be encapsulated. Further, capsule formation aids improve the performance of the capsule delivery system by stabilizing capsules and/or their deposition to the target areas or releasing to the environment. Performance is measured by the intensity of the fragrance release during the pre-rub phase and post-rub. The pre-rub phase is the phase when the capsules have been deposited on the cloth, e.g., after a fabric softener containing capsules has been used during the wash cycle. The post-rub phase is after the capsules have been deposited and the capsules are broken by friction or other similar mechanisms.

In general, the amount of the capsule formation aid varies from 0.1 to 5% (e.g., 0.05 to 0.2%, 0.5 to 4%, 0.2 to 2%, 1 to 2%, or 1% to 3%) by weight of the capsule delivery system.

In some embodiments, the capsule formation aid is a protective colloid or emulsifier including, e.g., maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide and ethylene oxide, polyvinylpyrrolidone (PVP), polyvinyl alcohols (PVA), sodium salt of naphthalene sulfonate condensate, carboxymethyl cellulose (CMC), fatty acid esters of polyoxyethylenated sorbitol, sodium dodecylsulfate, and any combination thereof.

Commercially available surfactants include, but are not limited to, sulfonated naphthalene-formaldehyde condensates such as MORWET D425 (naphthalene sulfonate, Akzo Nobel, Fort Worth, Tex.); partially hydrolyzed polyvinyl alcohols such as MOWIOLs, e.g., MOWIOL 3-83 (Air Products); ethylene oxide-propylene oxide block copolymers or poloxamers such as PLURONIC, SYNPERONIC or PLURACARE materials (BASF); sulfonated polystyrenes such as FLEXAN II (Akzo Nobel); ethylene-maleic anhydride polymers such as ZEMAC (Vertellus Specialties Inc.); and Polyquaternium series such as Polyquaternium 11 ("PQ11;" a copolymer of vinyl pyrrolidone and quaternized dimethylaminoethyl methacrylate; sold by BASF as LUVIQUAT PQ11 AT 1).

In other embodiments, the capsule formation aid is a processing aid such as hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly (alkyl(meth)acrylate-co-(meth)acrylic acid), poly(acrylic acid-co-maleic acid)copolymer, poly(alkyleneoxide), poly (vinylmethylether), poly(vinylether-co-maleic anhydride), and the like, as well as poly-(ethyleneimine), poly((meth) acrylamide), poly(alkyleneoxide-co-dimethylsiloxane), poly (amino dimethylsiloxane), and the like, and their quaternized forms.

The capsule formation aid may also be used in combination with CMC, polyvinylpyrrolidone, polyvinyl alcohol, alkylnaphthalenesulfonate formaldehyde condensates, and/ or a surfactant during processing to facilitate capsule formation. Examples of surfactants that can be used in combination with the capsule formation aid include, but are not limited to, cetyl trimethyl ammonium chloride (CTAC), poloxamers such as PLURONICS (e.g., PLURONIC F127), PLURAFAC (e.g., PLURAFAC F127), or MIRANET-N, saponins such as QNATURALE (National Starch Food Innovation); or a gum Arabic such as Seyal or Senegal. In certain embodiments, the CMC polymer has a molecular weight range between about 90,000 Daltons to 1,500,000 Daltons, preferably between about 250,000 Daltons to 750,000 Daltons and more preferably between 400,000 Daltons to 750,000 Daltons. The CMC polymer has a degree of substitution between about 0.1 to about 3, preferably between about 0.65 to about 1.4, and more preferably between about 0.8 to about 1.0. The CMC polymer is present in the capsule slurry at a level from about 0.1% to about 2% and preferably from about 0.3% to about 0.7%. In other embodiments, polyvinylpyrrolidone used in this invention is a water-soluble polymer and has a molecular weight of 1,000 to 10,000,000. Suitable polyvinylpyrrolidone are polyvinylpyrrolidone K12, K15, K17, K25, K30, K60, K90, or a mixture thereof. The amount of polyvinylpyrrolidone is 2-50%, 5-30%, or 10-25% by weight of the capsule delivery system. Commercially available alkylnaphthalenesulfonate formaldehyde condensates include MORWET D-425, which is a sodium salt of naphthalene sulfonate condensate by Akzo Nobel, Fort Worth, Tex.

Chain Termination Agent. Polymerization reactions for forming polyurea/polyurethane polymers can be terminated by adding a chain termination agent, e.g., a monofunctional amine or alcohol. Further, a chain termination agent also reacts with isocyanate groups on the surface of the capsules, thus reduced/eliminated isocyanate groups. Examples of a chain termination agent include $C_1$-$C_{20}$ primary and secondary amines, $C_1$-$C_{20}$ alcohols, $C_1$-$C_{20}$ thiols, and any combination thereof.

Active Material. The core of the microcapsules of the invention can include one or more active materials including, but not limited to, a fragrance, pro-fragrance, flavor, malodor counteractive agent, anti-inflammatory agent, anesthetic, analgesic, anti-viral agent, anti-infectious agent, anti-acne agent, skin lightening agent, insect repellant, emollient, skin moisturizing agent, vitamin or derivative thereof, nanometer to micron size inorganic solid, polymeric or elastomeric particle, or combination thereof. Individual active materials that can be encapsulated include:

i) hydrocarbons, such as, for example, 3-carene, α-pinene, β-pinene, α-terpinene, γ-terpinene, p-cymene, bisabolene, camphene, caryophyllene, cedrene, farnesene, limonene, longifolene, myrcene, ocimene, valencene, (E,Z)-1,3,5-undecatriene, styrene, and diphenylmethane;

ii) aliphatic alcohols, such as, for example, hexanol, octanol, 3-octanol, 2,6-dimethyl-heptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol, aliphatic aldehydes and their acetals such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2,2,5-trimethyl-4-hexene, and citronellyl oxyacetaldehyde;

iii) aliphatic ketones and oximes thereof, such as, for example, 2-heptanone, 2-octanone, 3-octanone, 2-nonanone, 5-methyl-3-heptanone, 5-methyl-3-heptanone oxime, 2,4,4,7-tetra-methyl-6-octen-3-one, aliphatic sulfur-containing compounds, such as for example 3-methylthio-hexanol, 3-methylthiohexyl acetate, 3-mercaptohexanol, 3-mercapto-hexyl acetate, 3-mercapto-hexyl butyrate, 3-acetylthiohexyl acetate, 1-menthene-8-thiol, and aliphatic nitriles (e.g., 2-nonenenitrile, 2-tridecenenitrile, 2,12-tridecenenitrile, 3,7-dimethyl-2,6-octadienenitrile, and 3,7-dimethyl-6-octenenitrile);

iv) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

v) acyclic terpene alcohols, such as, for example, citronellol, geraniol, nerol, linalool, lavandulol, nerolidol, farnesol, tetrahydrolinalool, tetrahydrogeraniol, 2,6-dimethyl-7-octen-2-ol, 2,6-dimethyloctan-2-ol, 2-methyl-6-methylene-7-octen-2-ol, 2,6-dimethyl-5,7-octadien-2-ol, 2,6-dimethyl-3,5-octadien-2-ol, 3,7-dimethyl-4,6-octadien-3-ol, 3,7-dimethyl-1,5,7-octatrien-3-ol, 2,6-dimethyl-2,5,7-octatrien-1-ol, as well as formates, acetates, propionates, isobutyrates, butyrates, isovalerates, pentanoates, hexanoates, crotonates, tiglinates and 3-methyl-2-butenoates thereof;

vi) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, α-sinensal, β-sinensal, geranylacetone, as well as the dimethyl- and diethylacetals of geranial, neral and 7-hydroxy-3,7-dimethyloctanal;

vii) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, methan-8-ol, methan-1-ol, methan-7-ol, borneol, isoborneol, linalool oxide, nopol, cedrol, ambrinol, vetiverol, and guaiol;

viii) cyclic terpene aldehydes and ketones, such as, for example, menthone, isomenthone, 8-mercaptomenthan-3-one, carvone, camphor, fenchone, α-ionone, β-ionone, α-n-methylionone, β-n-methylionone, α-isomethylionone, β-isomethylionone, alpha-irone, α-damascone, β-damascone, β-damascenone, δ-damascone, γ-damascone, 1-(2,4,4-trimethyl-2-cyclohexen-1-yl)-2-buten-1-one, 1,3,4,6,7,8a-hexahydro-1,1,5,5-tetra-methyl-2H-2,4a-methanonaphthalen-8(5H-)-one, nootkatone, dihydronootkatone; acetylated cedarwood oil (cedryl methyl ketone);

ix) cyclic alcohols, such as, for example, 4-tert-butylcyclohexanol, 3,3,5-trimethylcyclo-hexanol, 3-isocamphylcyclohexanol, 2,6,9-trimethyl-Z2,Z5,E9-cyclo-dodecatrien-1-ol, 2-iso-butyl-4-methyltetrahydro-2H-pyran-4-ol;

x) cycloaliphatic alcohols, such as, for example, alpha, 3,3-trimethylcyclo-hexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

xi) cyclic and cycloaliphatic ethers, such as, for example, cineole, cedryl methyl ether, cyclododecyl methyl ether;

xii) (ethoxymethoxy)cyclododecane; alpha-cedrene epoxide, 3a,6,6,9a-tetramethyl-dodecahydronaphtho[2,1-b]furan, 3a-ethyl-6,6,9a-trimethyldodecahydro-naphtho[2,1-b]furan, 1,5,9-trimethyl-13-oxabicyclo[10.1.0]-trideca-4,8-diene, rose oxide, 2-(2,4-dimethyl-3-cyclohexen-1-yl)-5-methyl-5-(1-methylpropyl)-1,3-dioxan-;

xiii) cyclic ketones, such as, for example, 4-tert.-butyl-cyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert-pentylcyclohexanone, 5-cyclohexadecen-1-one, 6,7-dihydro-1,1,2,3,3-pentamethyl-4(5H)-indanone, 5-cyclohexadecen-1-one, 8-cyclohexa-decen-1-one, 9-cycloheptadecen-1-one, cyclopentadecanone, cycloaliphatic aldehydes, such as, for example, 2,4-dimethyl-3-cyclohexene carbaldehyde, 2-methyl-4-(2,2,6-trimethyl-cyclohexen-1-yl)-2-butenal, 4-(4-hydroxy-4-methylpentyl)-3-cyclohexene carbaldehyde, 4-(4-methyl-3-penten-1-yl)-3-cyclohexene carbaldehyde;

xiv) cycloaliphatic ketones, such as, for example, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-trimethyl-2,5,9-cyclododecatrienylketone, tert-butyl-(2,4-dimethyl-3-cyclohexen-1-yl)ketone;

xv) esters of cyclic alcohols, such as, for example, 2-tert-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl-isobutyrate, 4,7-methanooctahydro-5 or 6-indenyl acetate;

xvi) esters of cycloaliphatic carboxylic acids, such as, for example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

xvii) aromatic and aliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)-propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

xviii) esters of aliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethylphenylethyl acetate, alpha, alpha-dimethylphenylethyl butyrate, cinnamyl acetate, 2-phenoxyethyl isobutyrate, 4-methoxybenzyl acetate, aralphatic ethers, such as for example 2-phenylethyl methyl ether, 2-phenylethyl isoamyl ether, 2-phenylethyl-1-ethoxyethyl ether, phenylacetaldehyde dimethyl acetal, phenylacetaldehyde diethyl acetal, hydratropaaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

xix) aromatic and aliphatic aldehydes, such as, for example, benzaldehyde; phenylacetaldehyde, 3-phenylpropanal, hydratropaldehyde, 4-methylbenzaldehyde, 4-methyl-phenylacetaldehyde, 3-(4-ethylphenyl)-2,2-dimethylpropanal, 2-methyl-3-(4-isopropylphenyl)-propanal, 2-methyl-3-(4-tert-butylphenyl)propanal, 3-(4-tert-butylphenyl)propanal, cinnamaldehyde, alpha-butylcinnamaldehyde, alpha-amyl-cinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal;

xx) aromatic and aliphatic ketones, such as, for example, acetophenone, 4-methylaceto-phenone, 4-methoxyacetophenone, 4-tert-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert-butyl-1,1-dimethyl-4-indanyl methyl ketone, 1-[2,3-dihydro-1,1,2,6-tetramethyl-3-(1-methyl-ethyl)-1H-5-indenyl]ethanone, 5',6',7',8'-tetrahydro-3',5',5',6',8',8'-hexamethyl-2-aceto-naphthone;

xxi) aromatic and araliphatic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenonitrile, 5-phenyl-3-methylpentano-nitrile, methyl anthranilate, methy-N-methylanthranilate, Schiff's bases of methyl anthranilate with 7-hydroxy-3,7-dimethyl-octanal, 2-methyl-3-(4-tert-butylphenyl)-propanal or 2,4-dimethyl-3-cyclohexene carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin;

xxvi) essential oils, concretes, absolutes, resins, resinoids, balsams, tinctures such as for example ambergris tincture, amyris oil, angelica seed oil, angelica root oil, aniseed oil, valerian oil, basil oil, tree moss absolute, bay oil, armoise oil, benzoe resinoid, bergamot oil, beeswax absolute, birch tar oil, bitter almond oil, savory oil, buchu leaf oil, cabreuva oil, cade oil, calamus oil, camphor oil, cananga oil, cardamom oil, cascarilla oil, cassia oil, cassie absolute, castoreum absolute, cedar leaf oil, cedar wood oil, cistus oil, citronella oil, lemon oil, copaiba balsam, copaiba balsam oil, coriander oil, costus root oil, cumin oil, cypress oil, davana oil, dill weed oil, dill seed oil, eau de brouts absolute, oakmoss absolute, elemi oil, estragon oil, *Eucalyptus citriodora* oil, *Eucalyptus* oil (cineole type), fennel oil, fir needle oil, galbanum oil, galbanum resin, geranium oil, grapefruit oil, guaiacwood oil, gurjun balsam, gurjun balsam oil, helichrysum absolute, helichrysum oil, ginger oil, iris root absolute, iris root oil, jasmine absolute, calamus oil, blue camomile oil, Roman camomile oil, carrot seed oil, cascarilla oil, pine needle oil, spearmint oil, caraway oil, labdanum oil, labdanum absolute, labdanum resin, lavandin absolute, lavandin oil, lavender absolute, lavender oil, lemongrass oil, lovage oil, lime oil distilled, lime oil expressed, linaloe oil, *Litsea cubeba* oil, laurel leaf oil, mace oil, marjoram oil, mandarin oil, massoi (bark) oil, mimosa absolute, ambrette seed oil, musk tincture, clary sage oil, nutmeg oil, myrrh absolute, myrrh oil, myrtle oil, clove leaf oil, clove bud oil, neroli oil, olibanum absolute, olibanum oil, opopanax oil, orange flower absolute, orange oil, origanum oil, palmarosa oil, patchouli oil, perilla oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, Dalmatian sage oil, Spanish sage oil, sandal-wood oil, celery seed oil: spike-lavender oil, star anise oil, storax oil, tagetes oil, fir needle oil, tea tree oil, turpentine oil, thyme oil, Tolu balsam, tonka bean absolute, tuberose absolute, vanilla extract, violet leaf absolute, verbena oil, vetiver oil, juniperberry oil, wine lees oil, wormwood oil, wintergreen oil, ylang-ylang oil, hyssop oil, civet absolute, cinnamon leaf oil, cinnamon bark oil, and fractions thereof or ingredients isolated therefrom;

xxvii) flavors including, but are not limited to, acetaldehyde, dimethyl sulfide, ethyl acetate, ethyl propionate, methyl butyrate, and ethyl butyrate. Flavors containing volatile aldehydes or esters include, e.g., cinnamyl acetate, cinnamaldehyde, citral, diethylacetal, dihydrocarvyl acetate, eugenyl formate, and p-methylanisole. Further examples of volatile compounds that may be present in the instant flavor oils include acetaldehyde (apple); benzaldehyde (cherry, almond); cinnamic aldehyde (cinnamon); citral, i.e., alpha citral (lemon, lime); neral, i.e., beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e., trans-2 (berry fruits); tolyl aldehyde (cherry, almond); veratraldehyde (vanilla); 2,6-dimethyl-5-heptenal, i.e., melonal (melon); 2-6-dimethyloctanal (green fruit); and 2-dodecenal (citrus, mandarin); cherry; or grape and mixtures thereof. The composition may also contain taste modulators and artificial sweeteners. As used herein, flavor is understood to include spice oleoresins derived from allspice, basil, *capsicum*, cinnamon, cloves, cumin, dill, garlic, marjoram, nutmeg, paprika, black pepper, rosemary, and turmeric, essential oils, anise oil, caraway oil, clove oil, *Eucalyptus* oil, fennel oil, garlic oil, ginger oil, peppermint oil, onion oil, pepper oil, rosemary oil, spearmint oil, citrus oil, orange oil, lemon oil, bitter orange oil, tangerine oil, alliaceous flavors, garlic, leek, chive, and onion, botanical extracts, arnica flower extract, chamomile flower extract, hops extract, marigold extract, botanical flavor extracts, blackberry, chicory root, cocoa, coffee, kola, licorice root, rose hips, sarsaparilla root, sassafras bark, tamarind and vanilla extracts, protein hydrolysates, hydrolyzed vegetable proteins, meat protein hydrolyzes, milk protein hydrolyzates and compounded flavors both natural and artificial including those disclosed in S. Heath, Source Book of Flavors, Avi Publishing Co., Westport Conn., 1981, pages 149-277. Specific preferred flavor adjuvants include, but are not limited to, the following: anise oil; ethyl-2-methyl butyrate; vanillin; cis-3-heptenol; cis-3-hexenol; trans-2-heptenal; butyl valerate; 2,3-diethyl pyrazine; methylcyclo-pentenolone; benzaldehyde; valerian oil; 3,4-dimeth-oxyphenol; amyl acetate; amyl cinnamate, γ-butyryl lactone; furfural; trimethyl pyrazine; phenyl acetic acid; isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; γ-hexenyl lactone; 2,4-decadienal; 2,4-heptadienal; methyl thiazole alcohol (4-methyl-5-b-hydroxyethyl thiazole); 2-methyl butanethiol; 4-mercapto-2-butanone; 3-mercapto-2-pentanone; 1-mercapto-2-propane; benzaldehyde; furfural; furfuryl alcohol; 2-mercapto propionic acid; alkyl pyrazine; methyl pyrazine; 2-ethyl-3-methyl pyrazine; tetramethyl pyrazine; polysulfides; dipropyl disulfide; methyl benzyl disulfide; alkyl thiophene; 2,3-dimethyl thiophene; 5-methyl furfural; acetyl furan; 2,4-decadienal; guiacol; phenyl acetaldehyde; decalactone; D-limonene; acetoin; amyl acetate; maltol; ethyl butyrate; levulinic acid; piperonal; ethyl acetate; n-octanal; n-pentanal; n-hexanal; diacetyl; monosodium glutamate; monopotassium glutamate; sulfur-containing amino acids, e.g., cysteine; hydrolyzed vegetable protein; 2-methylfuran-3-thiol; 2-methyldihydrofuran-3-thiol; 2,5-dimethylfuran-3-thiol; hydrolyzed fish protein; tetramethyl pyrazine; propylpropenyl disulfide; propylpropenyl trisulfide; diallyl disulfide; diallyl trisulfide; dipropenyl disulfide; dipropenyl trisulfide; 4-methyl-2-[(methylthio)-ethyl]-1,3-dithiolane; 4,5-dimethyl-2-(methylthiomethyl)-1,3-dithiolane; 4-methyl-2-(methylthiomethyl)-1,3-dithiolane, and the flavor ingredients described in U.S. Pat. Nos. 6,110,520 and 6,333,180;

xxviii) taste masking agents, substances for masking one or more unpleasant taste sensations, in particular a bitter, astringent and/or metallic taste sensation or aftertaste. Examples include lactisol [2O-(4-methoxyphenyl) lactic acid] (see U.S. Pat. No. 5,045,336), 2,4-dihydroxybenzoic acid potassium salt (see U.S. Pat. No. 5,643,941), ginger extracts (see GB 2,380,936), neohesperidine dihydrochalcone (see *Manufacturing Chemist* (2000) 71:16-17), specific flavones (2-phenylchrom-2-en-4-ones) (see U.S. Pat. No. 5,580,545), specific nucleotides, for example cytidine-5'-monophosphates (CMP) (see US 2002/0177576), specific sodium salts, such as sodium chloride, sodium citrate, sodium acetate and sodium lactate (see Breslin & Beauchamp (1997) *Nature* 387:563), a lipoprotein of O-lactoglobulin and phosphatidic acid (see EP 635218), neodiosmine [5,7-dihydroxy-2-(4-methoxy-3-hydroxyphenyl)-7-O-neohesperidosyl-chrom-2-en-4-one] (see U.S. Pat. No. 4,154,862), preferably hydroxyflavanones according to EP 1258200, in turn preferred in this respect 2-(4-hydroxyphenyl)-5,7-dihydroxychroman-4-one (naringenin), 2-(3,4-dihydroxy-phenyl)-5,7-dihydroxychroman-4-one (eriodictyol), 2-(3,4-dihydroxyphenyl)-5-hydroxy-7-methoxychroman-4-one (eriodictyol-7-methylether), 2-(3,4-dihydroxyphenyl)-7-hydroxy-5-methoxychroman-4-one (eriodictyol-5-methylether) and 2-(4-hydroxy-3-methoxyphenyl)-5,7-dihydroxychroman-4-one (homoeriodictyol), the (2S)- or (2R)-enantiomers thereof or mixtures thereof as well as the mono- or polyvalent phenolate salts thereof with $Na^+$, $K^+$, $NH4^+$, $Ca^{2+}$, $Mg^{2+}$ or $Al^{3+}$ as counter cations or γ-aminobutyric acid (4-aminobutyric acid, as the neutral form ("inner salt") or in the carboxylate or ammonium form) according to WO 2005/09684;

xxix) taste sensates including hot tasting, salivation-inducing substances, substances causing a warmth or tingling feeling, and cooling active ingredients. Examples of hot tasting and/or salivation-inducing substances and/or substances which cause a feeling of warmth and/or a tingling feeling on the skin or on the mucous membranes and which can be a constituent of the products according to the invention are: capsaicin, dihydrocapsaicin, gingerol, paradol, shogaol, piperine, carboxylic acid-N-vanillylamides, in particular nonanoic acid-N-vanillylamide, pellitorin or spilanthol, 2-nonanoic acid amides, in particular 2-nonanoic acid-N-isobutylamide, 2-nonanoic acid-N-4-hydroxy-3-methoxyphenylamide, alkyl ethers of 4-hydroxy-3-methoxybenzyl alcohol, in particular 4-hydroxy-3-methoxybenzyl-n-butylether, alkyl ethers of 4-acyloxy-3-methoxybenzyl alcohol, in particular 4-acetyloxy-3-methoxybenzyl-n-butylether and 4-acetyloxy-3-methoxybenzyl-n-hexylether, alkyl ethers of 3-hydroxy-4-methoxybenzyl alcohol, alkyl ethers of 3,4-dimethoxybenzyl alcohol, alkyl ethers of 3-ethoxy-4-hydroxybenzyl alcohol, alkyl ethers of 3,4-methylene dioxybenzyl alcohol, (4-hydroxy-3-methoxyphenyl)acetic acid amides, in particular (4-hydroxy-3-methoxyphenyl)acetic acid-N-n-octylamide, vanillomandelic acid alkylamides, ferulic acid-phenethylamides, nicotinaldehyde, methylnicotinate, propylnicotinate, 2-butoxyethylnicotinate, benzylnicotinate, 1-acetoxychavicol, polygodial and isodrimeninol, further preferred cis- and/or trans-pellitorin according to WO 2004/000787 or WO 2004/043906, alkenecarboxylic acid-N-alkylamides according to WO 2005/044778, mandelic acid alkylamides according to WO 03/106404 or alkyloxyalkanoic acid amides according to WO 2006/003210. Examples of preferred hot tasting natural extracts and/or natural extracts which cause a feeling of warmth and/or a tingling feeling on the skin or on the mucous membranes and which can be a constituent of the products according to the invention are: extracts of paprika, extracts of pepper (for example *capsicum* extract), extracts of chili pepper, extracts of ginger roots, extracts of *Afranomum melgueta*, extracts of *Spilanthes acmella*, extracts of *Kaempferia galangal* or extracts of *Alpinia galanga*. Suitable cooling active ingredients include the following: L-menthol, D-menthol, racemic menthol, menthone glycerol acetal (tradename: FRESCOLAT MGA), menthyl lactate preferably being L-menthyl lactate, in particular L-menthyl-L-lactate), substituted menthyl-3-carboxamides (for example menthyl-3-carboxylic acid-N-ethylamide), 2-isopropyl-N-2,3-trimethyl-butanamide, substituted cyclohexane carboxamides, 3-menthoxypropane-1,2-diol, 2-hydroxyethyl menthyl carbonate, 2-hydroxypropyl menthyl carbonate, N-acetylglycine menthyl ester, isopulegol, hydroxycarboxylic acid menthyl esters (for example menthyl-3-hydroxybutyrate), monomenthyl succinate, 2-mercaptocyclodecanone, menthyl-2-pyrrolidin-5-onecarboxylate, 2,3-dihydroxy-p-menthane, 3,3,5-trimethylcyclohexanone glycerol ketal, 3-menthyl-3,6-di- and -trioxaalkanoates, 3-menthyl methoxyacetate and icilin. Cooling active ingredients which are particularly preferred are as follows: L-menthol, racemic menthol, menthone glycerol acetal (tradename: FRESCOLAT MGA), menthyl lactate (preferably L-menthyl lactate, in particular L-menthyl-L-lactate (tradename: FRESCOLAT ML), 3-menthoxypropane-1,2-diol, 2-hydroxyethyl menthyl carbonate, 2-hydroxypropyl menthyl carbonate.

xxx) malodor counteracting agents including an α,β-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, nano silver, zinc undecenylate, β-naphthyl methyl ether, β-naphthyl ketone, benzyl acetone. They may include mixture of hexahydro-4,7-methanoinden-5-yl propionate and hexahydro-4,7-methanoinden-6-yl propionate; 4-(2,6,6-trimethyl-2-cyclohexen-1-yl)-3-methyl-3-buten-2-one; 3,7-dimethyl-2,6-nonadien-1-nitrile; dodeca-hydro-3a,6,6,9a-tetramethylnaphtho(2,1-b)furan; ethylene glycol cyclic ester of n-dodecanedioic acid; 1-cyclohexadecen-6-one; 1-cycloheptadecen-10-one; and corn mint oil. They may also include 1-cyclohexylethan-1-yl butyrate; 1-cyclohexylethan-1-yl acetate; 1-cyclohexylethan-1-ol; 1-(4'-methylethyl)cyclohexylethan-1-yl propionate; and 2'-hydroxy-1'-ethyl(2-phenoxy)acetate each of which compound is marketed under the trademark VEILEX by International Flavors & Fragrances Inc. More suitable malodor counteracting agents are polymers containing an α-keto, benzaldehyde, or α,β-unsaturated carbonyl moiety, such as those described in US Application Publications 2012/0294821, 2013/0101544 and 2013/0101545;

xxxi) vitamins including any vitamin, a derivative thereof and a salt thereof. Examples are as follows: vitamin A and its analogs and derivatives (e.g., retinol, retinal, retinyl palmitate, retinoic acid, tretinoin, and iso-tretinoin, known collectively as retinoids), vitamin E (tocopherol and its derivatives), vitamin C (L-ascorbic acid and its esters and other derivatives), vitamin B3 (niacinamide and its derivatives), alpha hydroxy acids (such as glycolic acid, lactic acid, tartaric acid, malic acid, citric acid, etc.) and beta hydroxy acids (such as salicylic acid and the like);

xxxii) antibacterials including bisguanidines (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol), triclosan (i.e., 2,4,4'-trichloro-2'-hydroxy-diphenylether), thymol, and triclocarban;

xxxiii) sunscreen actives including oxybenzone, octylmethoxy cinnamate, butylmethoxy dibenzoyln ethane, p-aminobenzoic acid and octyl dimethyl-p-aminobenzoic acid;

xxxiv) antioxidants such as beta-carotene, vitamin C (Ascorbic Acid) or an ester thereof, vitamin A or an ester thereof, vitamin B or an ester thereof, lutein or an ester thereof, lignan, lycopene, selenium, flavonoids, vitamin-like antioxidants such as coenzyme Q10 (CoQ10) and glutathione, and antioxidant enzymes such as superoxide dismutase (SOD), catalase, and glutathione peroxidase;

xxxv) anti-inflammatory agents including, e.g., methyl salicylate, aspirin, ibuprofen, and naproxen. Additional anti-inflammatories useful in topical applications include corticosteroids, such as, but not limited to, flurandrenolide, clobetasol propionate, halobetasol propionate, fluticasone propionate, betamethasone dipropionate, betamethasone benzoate, betamethasone valerate, desoximethasone, dexamethasone, diflorasone diacetate, mometasone furoate, amcinodine, halcinonide, fluocinonide, fluocinolone acetonide, desonide, triamcinolone acetonide, hydrocortisone, hydrocortisone acetate, fluoromethalone, methylprednisolone, and predinicarbate;

xxxvi) anesthetics that can be delivered locally including benzocaine, butamben, butamben picrate, cocaine, procaine, tetracaine, lidocaine and pramoxine hydrochloride;

xxxvii) analgesics such as ibuprofen, diclofenac, capsaicin, and lidocaine;

xxxviii) antifungal agents including, but not limited to, micanazole, clotrimazole, butoconazole, fenticonasole, tioconazole, terconazole, sulconazole, fluconazole, haloprogin, ketonazole, ketoconazole, oxinazole, econazole, itraconazole, torbinafine, nystatin and griseofulvin;

xxxix) antibiotics such as erythromycin, clindamycin, synthomycin, tetracycline, metronidazole and the like;

xl) anti-viral agents including famcyclovir, valacyclovir and acyclovir;

xli) anti-parasitic agents such as scabicedes, such as permethrin, crotamiton, lindane and ivermectin;

xlii) anti-infectious and anti-acne agents including benzoyl peroxide, sulfur, resorcinol and salicylic acid;

xliii) dermatological active ingredients useful in topical applications including, e.g., jojoba oil and aromatic oils such as methyl salicylate, wintergreen, peppermint oil, bay oil, *Eucalyptus* oil and citrus oils, as well as ammonium phenolsulfonate, bismuth subgallate, zinc phenolsulfonate and zinc salicylate;

xliv) enzymes and co-enzymes useful for topical application including co-enzyme Q10, papain enzyme, lipases, proteases, superoxide dismutase, fibrinolysin, desoxyribonuclease, trypsin, collagenase and sutilains;

xlv) skin whitening or lightening agents such as hydroquinone and monobenzone;

xlvi) anti-histamines including chlorpheniramine, bromopheniramine, dexchlorpheniramine, tripolidine, clemastine, diphenhydramine, prometazine, piperazines, piperidines, astemizole, loratadine and terfonadine;

xlvii) chemotherapeutic agents such as 5-fluorouracil, masoprocol, mechlorethamine, cyclophosphamide, vincristine, chlorambucil, streptozocin, methotrexate, bleomycin, dactinomycin, daunorubicin, coxorubicin and tamoxifen; and xlviii) insect repellents including pediculicides for treatment of lice, such as pyrethrins, permethrin, malathion, lindane and the like.

In addition to the active materials listed above, the microcapsules of this invention can also contain, for example, the following dyes, colorants or pigments: lactoflavin (riboflavin), beta-carotene, riboflavin-5'-phosphate, alpha-carotene, gamma-carotene, cantaxanthin, erythrosine, curcumin, quinoline yellow, yellow orange S, tartrazine, bixin, norbixin (annatto, orlean), capsanthin, capsorubin, lycopene, beta-apo-8'-carotenal, beta-apo-8'-carotenic acid ethyl ester, xantophylls (flavoxanthin, lutein, cryptoxanthin, rubixanthin, violaxanthin, rodoxanthin), fast carmine (carminic acid, cochineal), azorubin, cochineal red A (Ponceau 4 R), beetroot red, betanin, anthocyanins, amaranth, patent blue V, indigotine I (indigo-carmine), chlorophylls, copper compounds of chlorophylls, acid brilliant green BS (lissamine green), brilliant black BN, vegetable carbon, titanium dioxide, iron oxides and hydroxides, calcium carbonate, aluminum, silver, gold, pigment rubine BK (lithol rubine BK), methyl violet B, victoria blue R, victoria blue B, acilan brilliant blue FFR (brilliant wool blue FFR), naphthol green B, acilan fast green 10 G (alkali fast green 10 G), ceres yellow GRN, sudan blue II, ultramarine, phthalocyanine blue, phthalocayanine green, fast acid violet R. Further naturally obtained extracts (for example paprika extract, black carrot extract, red cabbage extract) can be used for coloring purposes. Goods results are also achieved with the colors named in the following, the so-called aluminum lakes: FD & C Yellow 5 Lake, FD & C Blue 2 Lake, FD & C Blue 1 Lake, Tartrazine Lake, Quinoline Yellow Lake, FD & C Yellow 6 Lake, FD & C Red 40 Lake, Sunset Yellow Lake, Carmoisine Lake, Amaranth Lake, Ponceau 4R Lake, Erythrosyne Lake, Red 2G Lake, Allura Red Lake, Patent Blue V Lake, Indigo Carmine Lake, Brilliant Blue Lake, Brown HT Lake, Black PN Lake, Green S Lake and mixtures thereof.

When the active material is a fragrance, it is preferred that fragrance ingredients within a fragrance having a C log P of 0.5 to 15 are employed. For instance, the ingredients having a C log P value between 0.5 and 8 (e.g., between 1 to 12, between 1.5 to 8, between 2 and 7, between 1 and 6, between 2 and 6, between 2 and 5, or between 3 and 7) are 25% or greater (e.g., 50% or greater and 90% or greater) by the weight of the fragrance.

In some embodiments, it is preferred that a fragrance having a weight-averaged C log P of 2.5 and greater (e.g., 3 or greater, 2.5 to 7, or 2.5 to 5) is employed. The weight-averaged C log P is calculated as follows:

$$C \log P = \{\text{Sum}[(Wi)(C \log P)i]\}/\{\text{Sum } Wi\},$$

in which Wi is the weight fraction of each fragrance ingredient and (C log P)i is the C log P of that fragrance ingredient.

As an illustration, it is preferred that greater than 60 weight percent, preferably greater than 80 and more preferably greater than 90 weight percent of the fragrance chemicals have C log P values of greater than 2, preferably greater than 3.3, more preferably greater than 4, and even more preferably greater than 4.5.

In other embodiments, the ingredients having a C log P value between 2 and 7 (e.g., between 2 and 6, and between 2 and 5) are 25% or greater (e.g., 50% or greater and 90% or greater) by the weight of the fragrance. In still other embodiments, it is preferred that greater than 60%, preferably greater than 80% and more preferably greater than 90% of the fragrance chemicals have Clog P values of greater than 3.3, preferably greater than 4 and most preferably greater than 4.5.

Those with skill in the art will appreciate that many fragrances can be created employing various solvents and fragrance chemicals. The use of a relatively low to intermediate C log P fragrance ingredients will result in fragrances that are suitable for encapsulation. These fragrances are generally water-insoluble, to be delivered through the capsule systems of this invention onto consumer products in different stages such as damp and dry fabric. Without encapsulation, the free fragrances would normally have evaporated or dissolved in water during use, e.g., wash. Though high log P materials are generally well delivered from a regular (non-encapsulated) fragrance in a consumer product, they have excellent encapsulation properties and are also suitable for encapsulation for overall fragrance character purposes, very long-lasting fragrance delivery, or overcoming incompatibility with the consumer product, e.g., fragrance materials that would otherwise be instable, cause thickening or discoloration of the product or otherwise negatively affect desired consumer product properties.

In some embodiments, the amount of encapsulated active material is from 5 to 95% (e.g., 20 to 90% or 40 to 85%) by weight of the microcapsule. The amount of the capsule wall is from 0.5% to 25% (e.g., 1.5 to 15% or 2.5 to 10%) also by weight of the microcapsule. In other embodiments, the amount of the encapsulated active material is from 15% to 99.5% (e.g., 50 to 98% or 30 to 95%) by weight of the microcapsule, and the amount of the microcapsule wall is from 0.5% to 85% (e.g., 2 to 50% or 5 to 70%) by weight of the microcapsule.

Adjunct Materials. In addition to the active materials, the present invention also contemplates the incorporation of adjunct materials including solvents, emollients, and core modifier materials in the core encapsulated by the capsule wall. Other adjunct materials are solubility modifiers, density modifiers, stabilizers, viscosity modifiers, pH modifiers, or any combination thereof. These modifiers can be present in the wall or core of the capsules, or outside the capsules in delivery system. Preferably, they are in the core as a core modifier.

The one or more adjunct material may be added in the amount of from 0.01% to 25% (e.g., from 0.5% to 10%) by weight of the capsule.

i) Preferable solvent materials are hydrophobic and miscible with the active materials. Solvents increase the compatibility of various active materials, increase the overall hydrophobicity of the mixture containing the active materials, influence the vapor pressure, or serve to structure the mixture. Suitable solvents are those having reasonable affinity for the active materials and a C log P greater than 2.5, preferably greater than 3.5 and more preferably greater than 5.5. In some embodiments, the solvent is combined with the active materials that have C log P values as set forth above. It should be noted that selecting a solvent and active material with high affinity for each other will result in improvement in stability. Exemplary solvents are triglyceride oil, mono and diglycerides, mineral oil, silicone oil, diethyl phthalate, polyalpha olefins, castor oil, isopropyl myristate, mono-, di- and tri-esters and mixtures thereof, fatty acids, and glycerine. The fatty acid chain can range from $C_4$-$C_{26}$ and can have any level of unsaturation. For instance, one of the following solvents can be used: capric/caprylic triglyceride known as NEOBEE M5 (Stepan Corporation); the CAPMUL series by Abitec Corporation (e.g., CAPMUL MCM); isopropyl myristate; fatty acid esters of polyglycerol oligomers, e.g., $R^2CO$—[$OCH_2$—$CH(OCOR^1)$—$CH^2O$—]$_n$, where $R^1$ and $R^2$ can be H or $C_4$-$C_{26}$ aliphatic chains, or mixtures thereof, and n ranges between 2 and 50, preferably 2 and 30; nonionic fatty alcohol alkoxylates like the NEODOL surfactants by BASF; the dobanol surfactants by Shell Corporation or the BIO-SOFT surfactants by Stepan, wherein the alkoxy group is ethoxy, propoxy, butoxy, or mixtures thereof and said surfactants can be end-capped with methyl groups in order to increase their hydrophobicity; di- and tri-fatty acid chain containing nonionic, anionic and cationic surfactants, and mixtures thereof; fatty acid esters of polyethylene glycol, polypropylene glycol, and polybutylene glycol, or mixtures thereof; polyalphaolefins such as the EXXONMOBIL PURESYM PAO line; esters such as the EXXONMOBIL PURESYN esters; mineral oil; silicone oils such polydimethyl siloxane and polydimethylcyclosiloxane; diethyl phthalate; di-octyl adipate and di-isodecyl adipate. In certain embodiments, ester oils have at least one ester group in the molecule. One type of common ester oil useful in the present invention are the fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like. A second type of useful ester oil is predominantly composed of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by FINETEX as FINSOLV are also suitable, as is ethylhexanoic acid glyceride. A third type of ester oil is liquid polyester formed from the reaction of a dicarboxylic acid and a diol. Examples of polyesters suitable for the present invention are the polyesters marketed by EXXONMOBIL under the trade name PURESYN ESTER. While the core can be free of the solvent, it is preferable that the level of solvent is 80 wt % or less, preferably 50 wt % or less (e.g., 0-20 wt %) by weight of the core.

ii) Triglycerides and modified triglycerides as emollients. These include vegetable oils such as jojoba, soybean, canola, sunflower, safflower, rice bran, avocado, almond, olive, sesame, persic, castor, coconut, and mink oils.

iii) Ester oils have at least one ester group in the molecule. One type of common ester oil useful in the present invention are the fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate.

iv) Ester oil as a liquid polyester formed from the reaction of a dicarboxylic acid and a diol. Examples of polyesters suitable for the present invention are the polyesters marketed by ExxonMobil under the trade name PURESYN ESTER®, hydrophobic plant extracts.

v) Silicones include, for example, linear and cyclic polydimethylsiloxanes, amino-modified, alkyl, aryl, and alkylaryl silicone oil.

vi) Low/non volatile hydrocarbons vii) Solid materials. Nanoscale solid particulate materials such as those disclosed in U.S. Pat. No. 7,833,960 may also be incorporated into the core and may be selected from, but not limited to, metal or metallic particles, metal alloys, polymer particles, wax particles, inorganic particulates, minerals and clay particles. The metal particles can be selected from a non-limiting list of main group elements, transition metal and post-transition metal elements including aluminum (Al), silica (Si), Titanium (Ti), chromium (Cr), manganese (Mn), iron (Fe), nickel (Ni), cobalt (Co), copper (Cu), gold (Au), silver (Ag), platinum (Pt) and palladium (Pd).

Polymer particles of any chemical composition and nature are suitable for the present invention as long as their physical dimension falls into the prescribed region and a liquid core is generated. The polymer particles can be selected from a nonlimiting list of polymers and co-copolymer based on polystyrene, polyvinyl acetate, polylactides, polyglycolides, ethylene maleic anhydride copolymer, polyethylene, polypropylene, polyamide, polyimide, polycarbonate, polyester, polyurethane, polyurea, cellulose and cellulose, and combinations and mixture of such polymers.

The inorganic particulate can be selected from a nonlimiting list including silica, titanium dioxide ($TiO_2$), zinc oxide (ZnO), $Fe_2O_3$, and other metal oxides such as but not limited to NiO, $Al_2O_3$, SnO, $SnO_2$, $CeO_2$, ZnO, CdO, $RuO_2$, FeO, CuO, AgO, $MnO_2$, as well as other transition metal oxides.

Examples of nanoscaled material include AEROSIL R812, which has a particle size of less than 25 nm according to the specification from the manufacture, Degussa Corp. Other suitable materials from Degussa include, but not limited to, AEROSIL R972, AEROSIL R974, AEROSIL R104, AEROSIL R106, AEROSIL R202, AEROSIL R805, AEROSIL R812, AEROSIL R812S, AEROSIL R816, AEROSIL R7200, AEROSIL R9200, and AEROXIDE TiO2 P25, AEROXIDE T805, AEROXIDE LE1, AEROXIDE LE2, AEROXIDE TiO2 NKT 90, AEROXIDE Alu C805, titanium dioxide PF2, SIPERNAT D110, SIPERNAT D-380. The hydrophobic materials from Deguassa Corp. such as including AEROSILE R812 and R972 are especially preferred.

Nanoscaled materials such as UVINUL $TiO_2$ and Z-COTE HP1 manufactured by BASF can also be used as well as and TI-PURE titanium dioxide, TI-PURE R-700, and TI-SELECT. Additional suitable materials include TS-6200 from Dupont and ZEROFREE 516, HUBERDERM 2000 and HUBERDERM 1000 from the J.M. Huber Corporation, Havre De Grace, Md. Silica products such as SYLOID 63, 244, 72, 63FP 244FP, 72FP, SYLOX 15, 2 and Zeolites such as SYLOSIV A3, SYLOSIV A4 and SYLOSIV K300 from Grace Davison can also be used.

viii) Polymeric core modifiers. Polymeric core modifiers are also contemplated. It has been found that the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion. Polymeric core modifiers include copolymers of ethylene; copolymers of ethylene and vinyl acetate (ELVAX polymers by DOW Corporation); copolymers of ethylene and vinyl alcohol (EVAL polymers by Kuraray); ethylene/acrylic elastomers such as VALNAC polymers by Dupont; polyvinyl polymers, such as polyvinyl acetate; alkyl-substituted cellulose, such as ethyl cellulose (ETHOCEL made by DOW Corporation) and hydroxypropyl celluloses (KLUCEL polymers by Hercules); cellulose acetate butyrate available from Eastman Chemical; polyacrylates (e.g., AMPHOMER, DEMACRYL LT and DERMACRYL 79, made by National Starch and Chemical Company, the AMERHOLD polymers by Amerchol Corporation, and ACUDYNE 258 by ISP Corporation); copolymers of acrylic or methacrylic acid and fatty esters of acrylic or methacrylic acid such as INTELIMER POLYMERS made by Landec Corporation (see also U.S. Pat. Nos. 4,830,855, 5,665,822, 5,783,302, 6,255,367 and 6,492,462); polypropylene oxide; polybutylene oxide of poly(tetrahydrofuran); polyethylene terephthalate; polyurethanes (DYNAM X by National Starch); alkyl esters of poly(methyl vinyl ether); maleic anhydride copolymers, such as the GANTREZ copolymers and OMNIREZ 2000 by ISP Corporation; carboxylic acid esters of polyamines, e.g., ester-terminated polyamides (ETPA) made by Arizona Chemical Company; polyvinyl pyrrolidone (LUVISKOL series of BASF); block copolymers of ethylene oxide, propylene oxide and/or butylenes oxide including, e.g., PLURONIC and SYNPERONIC polymers/dispersants by BASF. Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

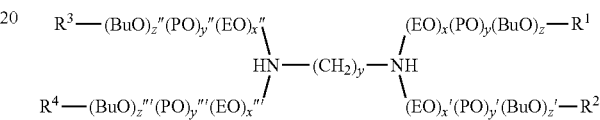

where $R^1$, $R^2$, $R^3$, and $R^4$ are independently H or any alkyl or fatty alkyl chain group. Examples of such polymers are the commercially known as TETRONICS by BASF Corporation.

ix) Sacrificial core ingredients. These ingredients can also be included in the core and are designed to be lost during or after manufacture and include, but are not limited to, highly water soluble or volatile materials.

x) Solubility modifiers. Nonlimiting examples of a solubility modifier include surfactants (e.g., SLS and TWEEN 80), acidic compounds (e.g., mineral acids such as sulfuric acid, hydrochloric acid, nitric acid, and phosphoric acid, and carboxylic acids such as acetic acid, citric acid, gluconic acid, glucoheptonic acid, and lactic acid), basic compounds (e.g., ammonia, alkali metal and alkaline earth metal hydroxides, primary, secondary, or tertiary amines, and primary, secondary, or tertiary alkanolamines), ethyl alcohol, glycerol, glucose, galactose, inositol, mannitol, glactitol, adonitol, arabitol, and amino acids.

xi) Density modifiers. The density of the capsule slurry and/or the oil core can be adjusted so that the capsule composition has a substantially uniform distribution of the capsules using known density modifiers or technologies such as those described in Patent Application Publications WO 2000/059616, EP 1502646, and EP 2204155. Suitable density modifiers include hydrophobic materials and materials having a desired molecular weight (e.g., higher than about 12,000), such as silicone oils, petrolatums, vegetable oils, especially sunflower oil and rapeseed oil, and hydrophobic solvents having a desired density (e.g., less than about 1,000 Kg/m$^3$ at 25° C., such as limonene and octane.

xii) Stabilizers. In some embodiments, a stabilizer (e.g., a colloidal stabilizer) is added to a capsule delivery system to stabilize the emulsion and/or capsule slurry. Examples of colloidal stabilizers are polyvinyl alcohol, cellulose derivatives such hydroxyethyl cellulose, polyethylene oxide, copolymers of polyethylene oxide and polyethylene or polypropylene oxide, or copolymers of acrylamide and acrylic acid. In other embodiments, a stabilizing agent (i.e., a stabilizer) is added to the capsule delivery system to improve the stability of the delivery system for an extended period of storage. When one of these delivery system is added to a consumer product such as a liquid fabric softener/freshener and liquid detergent, this delivery system will also improve the viscosity stability of the consumer product, thus extend the shelf life of the product.

Useful stabilizing agents include multi-functional amines, amino acids/peptides, mono-functional amines, polymers, and a polymeric mixture. These stabilizing agents are in presence in the compositions as free compounds, which are not covalently attached to the capsule walls, being part of the capsule walls, or encapsulated in capsules.

Multi-functional amines are those having at least an amine group (primary, secondary, or tertiary) and one or more other functional groups such as an amine and hydroxyl group. Exemplary multi-functional amines include hexamethylenediamine, hexaethylenediamine, ethylenediamine, 1,3-diaminopropane, 1,4-diamino-butane, diethylenetriamine, pentaethylenehexamine, bis(3-aminopropyl)amine, bis(hexan-ethylene)triamine, tris(2-aminoethyl)amine, triethylene-tetramine, N,N'-bis(3-amino-propyl)-1,3-propanediamine, tetraethylenepentamine, amino-2-methyl-1-propanol branched polyethylenimine, chitosan, 1,3-diaminoguanidine, 1,1-dimethylbiguanide, and guanidine. Suitable amino acids/peptides include arginine, lysine, histidine, ornithine, nisin, and gelatin. Suitable stabilizing polymers include polyvinylpyrrolidone, polyvinylpyridine-N-oxide, and polyvinyl imidazolinium. These polymers sometimes are used in combination with a second polymer (e.g., a block copolymer) such that the second polymer.

Monofunctional amines have a single amine group. Examples include $C_1$-$C_{20}$ primary, secondary, or tertiary amines, each of which typically has a molecular weight of 30 to 800 Daltons (e.g., 31 to 500 Daltons and 31 to 300 Daltons). They can be linear, branched, cyclic, acyclic, saturated, unsaturated, aliphatic, and/or aromatic. Nonlimiting examples are methylamine, dimethylamine, trimethylamine, ethylamine, diethylamine, triethylamine, propylamine, isopropylamine, butylamine, dodecylamine, tetradecylamine, aniline, 4-methylaniline, 2-nitroaniline, diphenyl amine, pyrrolidone, piperidine, and morpholine.

The stabilizing agent in the capsule composition can be present in an amount effective to stabilize the composition and/or the final consumer product containing the composition. This amount can be 1 ppm or greater (e.g., 20 ppm or greater, 20 ppm to 20%, 50 ppm to 10%, 50 ppm to 2%, 50 ppm to 1%, 50 to 2000 ppm, and 50 to 1000 ppm). Its concentration in a consumer product can be 20 ppm to 2% (e.g., 50 ppm to 2%, 50 ppm to 1%, 50 to 2000 ppm, or 50 to 1000 ppm).

xiii) Viscosity control agents. Viscosity control agents (e.g., suspending agents), which may be polymeric or colloidal (e.g., modified cellulose polymers such as methylcellulose, hydoxyethylcellulose, hydrophobically modified hydroxyethylcellulose, and cross-linked acrylate polymers such as Carbomer, hydrophobically modified polyethers) can be included in the capsule core or wall. Optionally, silicas, either hydrophobic or hydrophilic, can be included at a concentration from about 0.01% to about 20%, more preferable from 0.5% to about 5%, by the weight of the capsule composition. Examples of hydrophobic silicas include silanols, surfaces of which are treated with halogen silanes, alkoxysilanes, silazanes, and siloxanes, such as SIPERNAT D17, AEROSIL R972 and R974 available from Degussa. Exemplary hydrophilic silicas are AEROSIL 200, SIPERNAT 22S, SIPERNAT 50S (available from Degussa), and SYLOID 244 (available from Grace Davison).

xiv) Humectants. One or more humectants are optionally included to hold water in the capsule composition for a long period of time. Examples include glycerin, propylene glycol, alkyl phosphate esters, quaternary amines, inorganic salts (e.g., potassium polymetaphosphate, sodium chloride, etc.), polyethylene glycols, and the like.

Further suitable humectants, as well as viscosity control/suspending agents, are disclosed in U.S. Pat. Nos. 4,428,869, 4,464,271, 4,446,032, and 6,930,078. Details of hydrophobic silicas as a functional delivery vehicle of active materials other than a free flow/anticaking agent are disclosed in U.S. Pat. Nos. 5,500,223 and 6,608,017.

xv) pH modifiers. In some embodiments, one or more pH modifiers are included in the capsule composition to adjust the pH value of the capsule slurry and/or the capsule cores. The pH modifiers can also assist in the formation of capsule walls by changing the reaction rate of the cross-linking reactions that form the capsule walls. Exemplary pH modifiers include metal hydroxides (e.g., LiOH, NaOH, KOH, and $Mg(OH)_2$), metal carbonates and bicarbonates ($CsCO_3$ $Li_2CO_3$, $K_2CO_3$, $NaHCO_3$, and $CaCO_3$), metal phosphates/hydrogen phosphates/dihydrogen phosphates, metal sulfates, ammonia, mineral acids (HCl, $H_2SO_4$, $H_3PO_4$, and $HNO_3$), carboxylic acids (e.g., acetic acid, citric acid, lactic acid, benzoic acid, and sulfonic acids), and amino acids.

The level of the adjunct materials can be present at a level of 0.01 to 25% (e.g., from 0.5% to 10%) or greater than 10% (e.g., greater than 30% and greater than 70%).

Second Deposition Aid. In addition to the deposition protein of this invention, the microcapsule can further include a second deposition aid, e.g., one or more anionically, cationically, nonionically, or amphoteric water-soluble polymers, which is coated on the microcapsules before, during or after coating the microcapsules with the deposition protein. In particular embodiments, the second deposition aid is used in combination with microcapsules coated with a protein-silanol copolymer, protein-silane copolymer, protein-siloxane copolymer, and a combination thereof. Those skilled in the art would appreciate that the charge of these polymers can be adjusted by changing the pH, depending on the product in which this technology is to be used. Any suitable method for coating the deposition aids onto the encapsulated fragrance materials can be used. The nature of suitable polymers for assisted capsule delivery to interfaces depends on the compatibility with the capsule wall chemistry since there has to be some association to the capsule wall. This association can be through physical interactions, such as hydrogen bonding, ionic interactions, hydrophobic interactions, electron transfer interactions or, alternatively, the polymer coating could be chemically (covalently) grafted to the capsule or particle surface. Chemical modification of the capsule or particle surface is another way to optimize anchoring of the polymer coating to capsule or particle surface. Furthermore, the capsule and the polymer need to be compatible with the chemistry (polarity, for instance) of the desired interface. Therefore, depending on which capsule chemistry and interface (e.g., cotton, polyester, hair, skin, wool), the second deposition aid can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, polyaromatic, poly heterocyclic, or polylonene, with molecular weight (MW) ranging from about 1,000 to about 1,000,000,000, preferably from about 5,000 to about 10,000,000. As used herein, molecular weight is provided as weight average molecular weight.

Particular examples of cationic polymers that can be used as the second deposition aid include, e.g., polysaccharides such as guar, alginates, starch, xanthan, chitosan, cellulose, dextrans, arabic gum, carrageenan, and hyaluronates. These polysaccharides can be employed with cationic modification and alkoxy-cationic modifications such as cationic hydroxyethyl or cationic hydroxypropyl. For example, cationic reagents of choice are 3-chloro-2-hydroxypropyl trimethylammonium chloride or its epoxy version. Another example is graft-copolymers of polyDADMAC on cellulose. Alternatively, polysaccharides can be employed with aldehyde, carboxyl, succinate, acetate, alkyl, amide, sulfonate, ethoxy, propoxy, butoxy, and combinations of these functionalities; or any hydrophobic modification (compared to the polarity of the polysaccharide backbone). The above modifications can be in any ratio and the degree of functionalization can be up to complete substitution of all functionalizable groups, as long as the theoretical net charge of the polymer is zero (mixture of cationic and anionic functional groups) or preferably positive. Furthermore, up to five different types of functional groups may be attached to the polysaccharides. Also, polymer graft chains may be differently modified to the backbone. The counterions can be any halide ion or organic counter ion. See U.S. Pat. Nos. 6,297,203 and 6,200,554.

Another source of cationic polymers contain protonatable amine groups so that the overall net charge is zero (amphoteric: mixture of cationic and anionic functional groups) or positive. The pH during use will determine the overall net charge of the polymer. Examples include unmodified silk protein, zein, gelatin, keratin, collagen and any polypeptide, such as polylysine.

Further cationic polymers include polyvinyl polymers with up to five different types of monomers can be used. The monomers of such polymer have the generic formula:

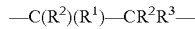

wherein, $R^1$ is H, $C_1$-$C_{25}$ alkane, $C_1$-$C_{25}$ alkene (in which the number of double bonds ranges from 1-5), $C_1$-$C_{25}$ alkoxylated fatty alcohol, or a liquid crystalline moiety that can provide the polymer with thermotropic liquid crystalline properties; $R^2$ is H or $CH_3$; and $R^3$ is —Cl, —$NH_2$ (i.e., polyvinyl amine or its copolymers with N-vinyl formamide.

Such polyvinyl polymers are sold under the name LUPAMIN 9095 by BASF Corporation. Further suitable cationic polymers containing hydroxyalkylvinylamine units, as disclosed in U.S. Pat. No. 6,057,404.

Another class of materials of use as second deposition aids are polyacrylates with up to five different types of monomers. Monomers of polyacrylates have the generic formula:

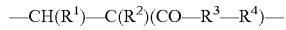

wherein, $R^1$ is H, $C_1$-$C_{25}$ alkane, $C_1$-$C_{25}$ alkene (in which the number of double bonds ranges from 1-5), $C_1$-$C_{25}$ alkoxylated fatty alcohol, or a liquid crystalline moiety that can provide the polymer with thermotropic liquid crystalline properties; $R^2$ is H or $CH_3$; $R^3$ is a $C_1$-$C_{25}$ alkyl alcohol or an alkylene oxide with any number of double bonds, or $R^3$ may be absent such that the C=O bond is (via the C-atom) directly connected to $R^4$; and $R^4$ is —$NH_2$, —$NHR^1$, —$NR^1R^2$, —$NR^1R^2R^5$ (where $R^5$=$R^1$, $R^2$, or —$CH_2$—COOH or its salt), —NH—C(O)—, sulfobetaine, betaine, polyethylene oxide, poly(ethyleneoxide/propylene oxide/butylene oxide) grafts with any end group, H, OH, styrene sulfonate, pyridine, quatemized pyridine, alkyl-substituted pyrrolidone or pyridine, pyridine-N-oxide, imidazolinium halide, imidazolium halide, imidazol, piperidine, —$OR^1$, —OH, —COOH alkali salt, sulfonate, ethoxy sulphate, pyrrolidone, caprolactam, phenyl-$R^4$ or naphthalene-$R^6$, where $R^4$ and $R^6$ are $R^1$, $R^2$, $R^3$, sulfonic acid or its alkali salt or organic counter ion. Also, glyoxylated cationic polyacrylamides can be used. Typical polymers of choice are those containing the cationic monomer dimethylaminoethyl methacrylate (DMAEMA) or methacrylamidopropyl trimethyl ammonium chloride (MAPTAC). DMAEMA can be found in GAFQUAT and GAFFIX VC-713 polymers from ISP. MAPTAC can be found in BASF's LUVIQUAT PQ11 PN and ISP's GAFQUAT HS100.

Another group of polymers that can be used are those that contain cationic groups in the main chain or backbone. Included in this group are:

i) polyalkylene imines such as polyethylene imine, commercially available as LUPASOL from BASF. Any molecular weight and any degree of crosslinking of this polymer can be used in the present invention;

ii) ionenes as disclosed in U.S. Pat. Nos. 4,395,541 and 4,597,962;

iii) adipic acid/dimethyl amino hydroxypropyl diethylene triamine copolymers, such as CARTARETIN F-4 and F-23, commercially available from Sandoz;

iv) polymers of the general formula: —[N(CH$_3$)$_2$—(CH$_2$)$_x$—NH—(CO)—NH—(CH$_2$)$_y$—N(CH$_3$)$_2$—(CH$_2$)$_z$—O—(—CH$_2$)$_p$]$_n$—, with x, y, z, p=1-12, and n according to the molecular weight requirements. Examples are Polyquaternium-2 (MIRAPOL A-15), Polyquaternium-17 (MIRAPOL AD-1), and Polyquaternium-18 (MIRAPOL AZ-1). Other polymers include cationic polysiloxanes and cationic polysiloxanes with carbon-based grafts with a net theoretical positive charge or equal to zero (mixture of cationic and anionic functional groups). This includes cationic end-group functionalized silicones (i.e., Polyquaternium-80). Silicones with general structure: —Si($R^1$)($R^2$)—O—]$_x$—[Si($R^3$)($R^2$)—O—]$_y$,— where $R^1$ is any alkane from $C_1$-$C_{25}$ or H with number of double bonds from 0-5, aromatic moieties, polysiloxane grafts, or mixtures thereof. $R^1$ can also be a liquid crystalline moiety that can provide the polymer with thermotropic liquid crystalline properties. $R^2$ can be H or $CH_3$; and $R^3$ can be —$R^1$-$R^4$, where $R^4$ can be —$NH_2$, —$NHR^1$, —$NR^1R^2$, —$NR^1R^2R^5$ (where $R^5$=$R^1$, $R^2$, or —$CH_2$—COOH or its salt), —NH—C(O)—, —COOH, —COO— alkali salt, any $C_1$-$C_{25}$ alcohol, —C(O)—$NH_2$ (amide), —C(O)—N($R^2$)($R^{2"}$)($R^{2""}$), sulfobetaine, betaine, polyethylene oxide, poly(ethyleneoxide/propylene oxide/butylene oxide) grafts with any end group, H, —OH, styrene sulfonate, pyridine, quaternized pyridine, alkyl-substituted pyrrolidone or pyridine, pyridine-N-oxide, imidazolinium halide, imidazolium halide, imidazol, piperidine, pyrrolidone, caprolactam, sulfonate, ethoxysulphate phenyl-$R^6$ or naphthalene-$R^7$ where $R^6$ and $R^7$ are $R^1$, $R^2$, $R^3$, sulfonic acid or its alkali salt or organic counter ion. $R^3$ can also be —(CH$_2$)$_x$—O—CH$_2$—CH(OH)—CH$_2$—N(CH$_3$)$_2$—CH$_2$—COOH and its salts. Any mixture of these $R^3$ groups can be selected. X and y can be varied as long as the theoretical net charge of the polymer is zero (amphoteric) or positive. In addition, polysiloxanes containing up to five different types of monomeric units may be used. Examples of suitable polysiloxanes are found in U.S. Pat. Nos. 4,395,541, 4,597, 962 and 6,200,554. Another group of polymers that can be used to improve capsule/particle deposition are phospholipids that are modified with cationic polysiloxanes. Examples of these polymers are found in U.S. Pat. No. 5,849,313, WO 1995/18096A1 and EP 0737183B1.

Another class of polymers includes polyethylene oxide-co-propyleneoxide-co-butylene oxide polymers of any ethylene oxide/propylene oxide/butylene oxide ratio with cationic groups resulting in a net theoretical positive charge or equal to zero (amphoteric). Examples of such polymers are the commercially available TETRONIC brand polymers.

Suitable polyheterocyclic (the different molecules appearing in the backbone) polymers include the piperazine-alkylene main chain copolymers disclosed by Kashiki & Suzuki (1986) Ind. Eng. Chem. Fundam. 25:120-125.

Table 2 below shows polyquaternium polymers that can be used as deposition aids in this invention.

TABLE 2

| Poly-quaternium | Description | Commercial Product |
|---|---|---|
| 1 | Ethanol, 2,2',2''-nitrilotris-, polymer with 1,4-dichloro-2-butene and N,N,N',N'-tetramethyl-2-butene-1,4-diamine | POLYQUAD (Alcon) |
| 2 | Poly[bis(2-chloroethyl) ether-alt-1,3-bis[3-(dimethylamino)propyl]urea] | MIRAPOL A-15 |
| 4 | Hydroxyethyl cellulose dimethyl diallylammonium chloride copolymer; Diallyldimethylammonium chloride-hydroxyethyl cellulose copolymer | CELQUAT L-200, H-100, L-200 |
| 5 | Copolymer of acrylamide and quaternized dimethylammoniumethyl methacrylate | MERQUAT 5, RETEN (Hercules) |
| 6 | Poly(diallyldimethyl ammonium chloride) | MERQUAT 100, 106, MIRAPOL 100 |
| 7 | Copolymer of acrylamide and diallyldimethylammonium chloride | MERQUAT 550, 550L, 550PR, S, 7SPR, 740, 2200, MIRAPOL 550, POLYQUART 770/NA, CONDITIONEZE 7 |
| 8 | Methyl and Stearyl Dimethylaminoethyl Methacrylate Quaternized with Dimethyl Sulfate | |
| 9 | Polydimethylaminoethyl Methacrylate Quaternized with Methyl Bromide | |
| 10 | Quaternized hydroxyethyl cellulose | MERQUAT 10, CELQUAT SC-230M, SC-240C, SC-140C, UCARE Polymer |
| 11 | Copolymer of vinylpyrrolidone and quaternized dimethylaminoethyl methacrylate | LUVIQUAT PQ 11PN, GAFQUAT 775N, 440, 734, 775 |
| 12 | 2-Propenoic Acid, 2-Methyl-, Decahydro-1,4-Dimethyl-7-(1-Methylethyl)-1-Phenanthrenyl)Methyl Ester, Polymer with 2-(Diethylamino)Ethyl 2-Methyl-2-Propenoate and Ethyl 2-Methyl-2-Propenoate, compd. with Dimethyl Sulfate | |
| 13 | 2-Propenoic Acid, 2-Methyl-, 2-(Diethyl-amino)Ethyl Ester, Polymer with Ethyl 2-Methyl-2-Propenoate and 9-Octadecenyl 2-Methyl-2-Propenoate, compd. with Dimethyl Sulfate | |
| 14 | Ethanaminium, N,N,N-Trimethyl-2-[(2-Methyl-1-Oxo-2-Propenyl)Oxy]-, Methyl Sulfate, Homopolymer | |
| 15 | Ethanaminium, N,N,N-Trimethyl-2-[(2-Methyl-1-Oxo-2-Propenyl)Oxy]-, Chloride, Polymer with 2-Propenamide | ROHAGIT KF 720F (Rohm GmbH) |
| 16 | Copolymer of vinylpyrrolidone and quaternized vinylimidazole | LUVIQUAT FC 370, HM 552, Style, FC 550, Excellence |
| 17 | Poly(Oxy-1,2-Ethanediyl (Dimethyl-iminio)-1,3-propanediylimino(1,6-Dioxo-1,6-Hexanediyl)Imino-1,3-Propanediyl-(Dimethyliminio)-1,2-Ethanediyl Dichloride | MIRAPOL AD |
| 18 | Poly[oxy-1,2-ethanediyl(dimethyliminio)-1,3-propanediylimino-(1,6-dioxo-1,6-heptanediyl)imino-1,3-propanediyl-(dimethyliminio)-1,2-ethanediyl dichloride] | LUVIQUAT 500 |
| 19 | Ethenol, polymer with aminomethyloxirane | ARLATONE PQ-220 (ICI Americas) |
| 20 | Ethenyl octadecyl ether, polymer with aminomethyloxirane | ARLATONE PQ-225 |
| 22 | Copolymer of Acrylic Acid and Diallyldimethylammonium Chloride | MERQUAT 280, 281, 280SD, 295 |
| 24 | Cellulose, 2-[2-Hydroxy-3-(Trimethyl-ammonio)Propoxy]Ethyl Ether, Chloride (Similar to PQ-10) | QUATRISOFT Polymer LM-200 (Dow Chemical) |

TABLE 2-continued

| Poly-quaternium | Description | Commercial Product |
|---|---|---|
| 27 | Hexanediamide, N,N'-bis(3-(Dimethyl-amino)Propyl)-, Polymer with N,N'-bis(3-Dimethylamino)Propyl Urea and 1,1'-Oxybis(2-Chloroethane), Block | |
| 28 | Copolymer of vinylpyrrolidone and methacrylamidopropyl trimethylammonium | GAFQUAT HS-100, CONDITIONEZE NT-10 |
| 29 | Chitosan, 2,3-Dihydroxypropyl-2-Hydroxy-3-(Trimethylammonio)Propyl Ether, Chloride | Quaternized Chitosan |
| 30 | Ethanaminium, NCarboxymethyl)-N,N-Dimethyl-2-((2-Methyl-1-Oxo-2-Propenyl)Oxy)-, Inner Salt, Polymer with Methyl 2-Methyl-2-Propenoate | MEXOMERE PX (Chimex) |
| 31 | 2-Propenenitrile, Homopolymer, Hydrolyzed, Block, Reaction Products with N,N-Dimethyl-1,3-Propanediamine, Di-Et Sulfate-Quaternized | HYPAN QT100 (Lipo) |
| 32 | Poly(acrylamide 2-methacryloxyethyltrimethyl ammonium chloride) | COSMEDIA CTC (Cognis GmbH) - PQ-32 + other, SALCARE SC92 (Ciba Corp.) PQ-32 + other |
| 33 | Ethanaminium, N,N,N-Trimethyl-2-[1-Oxo-2-Propenyl)Oxy]-, Chloride, Polymer with 2-Propenamide | LANOQUAT DES-50, ULTIMER CG-200 (Nalco), SEPIGEL Quat33 (Seppic) - PQ-33 + other |
| 34 | Poly(diethyliminio-1,3-propanediyldimethyliminio-1,3-propanediyl dibromide) | MEXOMERE PAK (Chimex) |
| 35 | Ethanaminium, N-carboxymethyl-N,N-dimethyl-2-(2-methyl-1-oxo-2-propenyloxy)-, inner salt, polymer with N,N,N-trimethyl-2-(2-methyl-1-oxo-2-propenyloxy)ethanaminium methyl sulfate | PLEX 3074 L (Rohm GmbH) |
| 36 | 2-Propenoic Acid, 2-Methyl-, 2-(Dimethylamino)Ethyl Ester, Polymer with Methyl 2-Methyl-2-Propenoate, compd. with Dimethyl Sulfate | PLEX 4739L (Rohm GmbH) |
| 37 | N,N,N-Trimethyl-2-[(Methyl-1-Oxo-2-Propenyl)Oxy]Ethanaminium Chloride, Homopolymer | ULTRAGEL 300 (Cognis), SYNTHALEN CN, CR, CU (3V Group), SYNTRAN PC 5320 (Interpolymer) |
| 39 | 2-Propen-1-aminium, N,NDimethyl-N-2-Propenyl-, Chloride, Polymer with 2-Propenamide and 2-Propenoic Acid | MERQUAT 3940, PLUS-3330, PLUS-3331, 3331PR |
| 42 | Poly[oxyethylene(dimethyliminio)ethylene(dimethylimino)ethylene dichloride] | BUSAN 1507 (Buckman Labs) |
| 43 | polymeric quaternary ammonium salt formed from acrylamide, acrylamidopropyltrimonium chloride, 2-amidopropylacrylamide sulfonate, and DMAPA monomers | GENAMIN PQ 43 (Clariant Functional Chemicals), BOZEQUAT 4000 (Clariant) |
| 44 | Poly(2-oxopyrrolidin-1-ylethylene, 3-methylimidazolium-1-ylethylene methyl sulfate) | LUVIQUAT ULTRACARE, MS 370 (BASF), SOFTENOL PQ44 (Zdchimmer & Schwarz Italianat S.p.A) |
| 45 | Glycine, N-methyl-N- [2-[(2-methyl-1-oxo-2-propenyl)oxy]ethyl]-, polymer with 2-(dimethylamino)ethyl 2-methyl-2-propenoate, compound with dimethyl sulfate | PLEX 3073L (Rohm GmbH) |
| 46 | 1H-Imidazolium, 1-Ethenyl-3-Methyl-, Methyl Sulfate, Polymer with 1-Ethenyl-hexahydro-2H-Azepin-2-one and 1-Ethenyl-2-Pyrrolildinone | LUVIQUAT Hold |
| 47 | 1-Propanaminium, N,N,NTrimethyl-3-((2-Methyl-1-Oxo-2-Propenyl)Amino)-, Chloride, Polymer with Methyl 2-Propenoate and 2-Propenoic Acid | MERQUAT 2001, 2001N |
| 48 | Polymeric quaternary ammonium salt of formed from methacryloyl ethyl betaine, 2-hydroxyethyl methacrylate and methacryloyl ethyl trimethyl ammonium chloride | PLASCIZE L-450 (Goo Chemical) |
| 49 | polymeric quaternary ammonium salt formed by the reaction of methacryloyl ethyl betaine, PEG-9 methacrylate and methacryloyl ethyl trimethyl ammonium chloride | PLASCIZE L-440 (Goo Chemical) |

TABLE 2-continued

| Poly-quaternium | Description | Commercial Product |
|---|---|---|
| 50 | Carboxylatoethyldimethylammonioethyl 2-methyl-2-propenoate homopolymer | PLASCIZE L-401 (Goo Chemical) |
| 51 | 3,5,8-Triox-4-Phosphaundec-10-en-1-aminium, 4-Hydroxy-N,N,N,10-Tetramethyl-9-Oxo, Inner Salt, 4-Oxide, Polymer with Butyl 2-Methyl-2-Propenoate | LIPIDURE PMB (NOF) |
| 53 | Acrylic Acid/Acrylamide/Methacryl-amidopropyltrimonium Chloride Copolymer | MERQUAT 2003PR |
| 54 | Aspartic acid, polymer with C6-18 alkylamine, 3-dimethylaminopropylamine and sodium chloroacetate | Quilty-Hy (Mitsui) |
| 55 | 1-Dodecanaminium, N,NDimethyl-N-[3-[(2-Methyl-1-Oxo-2-Propenyl)-Amino-Propyl]-, Chloride, Polymer with N-[3-(Dimethylamino)Propyl]-2-Methyl-2-Propenamide and 1-Ethenyl-2-Pyrrolidinone | STYREZE W |
| 56 | 5-Isocyanato-1-(isocyanatomethyl)-1,3,3-trimethylcyclohexane, polymer with 1,3-butanediol and bis(2-hydroxyethyl)di-methylammonium methyl sulfate | HAIRROL UC-4 (Sanyo Chemical) |
| 57 | 12-Hydroxy-9(Z)-octadecenamidopropyl-trimethylammonium chloride, polymers with ricinus communis (castor) oil, isooctdecanoic acid and butandioic acid | ZENIGLOSS Q (Zenitech) |
| 58 | 2-Propenoic Acid, Methyl Ester, Polymer with 2,2-Bis[(2-Propenyloxy)Methyl]-1-Butanol and Diethenylbenzene, Reaction Products with N,N-Dimethyl-1,3-Propane-diamine, Chloromethane-Quaternized | LOWENOL Conditioner PWW (Lowenstein) - PQ-58 and Wheat Protein |
| 59 | Poly(20,25-dioxo-2,5,10,15,18-penta-methyl-10-(2-hydroxy-3-(3-phenyl-2-propenamido)propyldimethylammonio)pro-pyl)-10-azonia-1,4,7,13,16,19-hexaoxa-pentacosanediyl) chloride | CRODASORB UV-HPP (Croda, Inc.) - PQ-59 and Butylene Glycol |
| 60 | 9-Octadecenoic Acid, 12-Hydroxy-, [(2-Hydroxyethyl)-Imino]Di-2,1-Ethanediyl Ester, Polymer with 5-Isocyanato-1-(Isocyanatomethyl)-1,3,3-Trimethyl-cyclohexane, Compd. with Diethyl Sulfate | Polylipid PPI-RC (Alzo/Bernel) - PQ-60 and Propylene Glycol |
| 61 | 2-Methyl-2-propenoyloxyethyl N,N,N-trimethylammonioethyl phosphate inner salt, polymer with octadecyl 2-methyl-2-propenoate | LIPIDURE-S (NOF) |
| 62 | Polymeric quaternary ammonium salt of butyl methacrylate, polyethylene glycol methyl ether methacrylate, ethylene glycol dimethacrylate and 2-methacryloylethyl trimonium chloride with 2,2'-azobis(2-methyl propionamidine)dihydro-chloride | NANOAQUASOME (Amore Pacific/Kyung-do) |
| 63 | polymeric quaternary ammonium salt formed by acrylamide, acrylic acid and ethyltrimonium chloride acrylate | FINQUAT (Innospec), OCTACARE PQ63 (Innospec Edison, NJ), OF-308 (WSP Chemical & Technology) |
| 64 | 2-Methyl-2-propenoyloxyethyl N,N,N-trimethylammonioethyl phosphate inner salt, polymer with 2-hydroxy-3-(2-methyl-2-propenoyl)oxypropyltrimethyl-ammonium chloride | LIPIDURE-C (NOF) |
| 65 | 2-Methyl-2-propenoyloxyethyl N,N,N-trimethylammonioethyl phosphate inner salt, polymer with butyl 2-methyl-2-propenoate and sodium 2-methyl-2-propenoate | LIPIDURE-A (NOF) |
| 66 | 5-Isocyanato-1-(isocyanatomethyl)-1,3,3-trimethylcyclohexane, polymer with di(hydroxypolymethylene) benzene-dicarboxylate and ethylbis(2-hydroxy-ethyl)methylammonium ethyl sulfate | WBR-2925C (Taisei) - PQ-66 and Methyl Pyrrolidone |
| 67 | 2-Hydroxyethyl cellulose ether, reaction products with N,N,N-trimethyl-N-oxiranylmethylammonium chloride and N-dodecyl-N,N-dimethyl-N-oxiranylmethylammonium chloride | SOFTCAT (Dow Chemical) |
| 68 | 1-Ethenyl-2-pyrrolidinone, polymer with 1-ethenylimidazole and 1-ethenyl-3-methylimidazolium methyl sulfate | LUVIQUAT Supreme |

TABLE 2-continued

| Poly-quaternium | Description | Commercial Product |
|---|---|---|
| 69 | polymeric quaternary ammonium salt composed of vinyl caprolactam, vinylpyrrolidone, dimethylaminopropyl methacrylamide (DMAPA), and methacryloylaminopropyl lauryldimonium chloride | AQUASTYLE 100, 300 (ISP) |
| 70 | polymeric quaternary ammonium salt consisting of an ethoxylated, propoxylated stearyl amine condensed with adipic acid and dilinoleic acid and quaternized with dimethyl sulfate | LUSTREPLEX (Croda) |
| 71 | | COLAMOIST 300P (Colonial Chemical Inc) |
| 72 | polymeric quaternary ammonium salt of hydroxethylcellulose reacted with a coco-alkyl dimethyl ammonium substituted epoxide | MIRUSTYLE CP (Croda) |
| 73 | polymeric quaternary ammonium salt consisting of propyltrimonium chloride acrylamide, ethyltrimonium chloride methacrylate and dimethylacrylamide monomers; Propanaminium, N,N,N-trimethyl-3-(2-propenamido)-, chloride, polymer with N,N,N-trimethyl-2-(2-methyl-2-propenoyloxy)ethanaminium chloride and N,N-dimethyl-2-propenamide | DIAFORMER C-802, C-823 (Mitsubishi Chem), DIASLEEK C-802, C-823 (Mitsubishi Chem) |
| 74 | | MIRAPOL PB 20 (Rhodia) POLYCARE Boost (Rhodia) |
| 75 | O-(2-Hydroxy-2-trimethylammonio-propyl)starch chloride, reaction products with O-(3-dodecyldimethylammonio-2-hydroxypropyl)starch chloride | AMYLOMER Cat 220EMU (Grafe Chemie) |
| 76 | | Mirapol AT-1 (Rhodia) |
| 77 | Cocoglucoside Crosspolymer Hydroxypropyltrimonium Chloride | Colonial Poly SugaQuat TM-8610P (Colonial Chemical Inc) |
| 78 | Decylglucoside Crosspolymer Hydroxypropyl Laurdimonium Chloride | Colonial POLY SUGA Quat L-1010P (Colonial Chemical Inc) |
| 79 | Decylglucoside Crosspolymer Hydroxypropyl Steardimonium Chloride | Colonial POLY SUGA Quat S-1010P (Colonial Chemical Inc) |
| 80 | Laurylglucoside Crosspolymer Hydroxypropyl Laurdimonium Chloride | Colonial POLY SUGA Quat L-1210P (Colonial Chemical Inc) |
| 81 | Laurylglucoside Crosspolymer Hydroxypropyl Steardimonium Chloride | Colonial POLY SUGA Quat S-1210P (Colonial Chemical Inc) |
| 82 | Laurylglucoside Crosspolymer Hydroxypropyltrimonium Chloride | Colonial P POLY SUGA Quat TM-1218P (Colonial Chemical Inc) |
| 84 | polymeric quaternary ammonium salt of acrylamidopropyltrimethyl-ammonium chloride, trimethylaminoethyl methacrylate dimethylacrylamide and hydroxyethylmethacrylate | DIASLEEK C-824 (Mitsubishi Chemical) |
| 85 | polymeric quaternary ammonium salt of acrylamidopropyltrimethyl-ammonium chloride, dimethylacrylamide and hydroxyethylmethacrylate | DIASLEEK C-825 (Mitsubishi Chemical) |
| 86 | polymeric quaternary ammonium salt of vinylpyrrolidone, 1-methyl-3-vinylimidazoline chloride, vinylimidazole and methacrylic acid | LUVIGEL Advanced (BASF) |
| 87 | polymeric quaternary ammonium salt of vinylpyrrolidone, vinylimidazole and diallyldimethyl ammonium chloride | LUVIQUAT Sensation (BASF) |
| 88 | Poly(Dilinoleyldimonium hydroxypropyl)chlorides) | COLAQUAT PDQ (Colonial Chemical Inc) |
| 89 | polymeric quaternary ammonium salt prepared by the reaction of t-butyl acrylate, vinyl pyrolidone, dimethylaminopropyl methacrylamide, methacrylic acid and ethyldimethyl[2-[(2-methyl-1-oxoallyl)oxy]ammonium ethyl sulfate, neutralized with orthophosphoric acid | (BASF) |
| 90 | polymeric quaternary ammonium salt of acrylamide and hydroxyethylcellulose | HYMOQUAT AK325R (Hymo Corporation) |

TABLE 2-continued

| Poly-quaternium | Description | Commercial Product |
|---|---|---|
| | quaternized with diallyldimethyl ammonium chloride | |
| 91 | polymeric quaternary ammonium salt of hydroxypropyl methacrylate and polyethylene glycol methacrylate quaternized with ethyltrimonium chloride methacrylate | SYNTRAN 5500 (Interpolymer) - PQ-91 and PA |
| 92 | Glycerylamidoethyl Methacrylate/Stearyl Methacrylate Copolymer | CERACUTE-G (NOF) |
| 94 | polymeric quaternary ammonium salt consisting of acrylamide, dimethyl diallyl ammonium chloride and methacrylamidopropyltrimonium chloride monomers | (Toho) |
| 95 | copolymer of Zea Mays (Corn) Starch, Acrylic Acid and acrylamidopropyl trimethylammonium chloride monomers | POLYQUART Ecoclean (Cognis) |
| 98 | | (Cognis GmbH) |
| 101 | | DEPOSILK Q1 (Air Products) |

Other suitable second deposition aids include those described in US 2013/0330292, US 2013/0337023, US 2014/0017278.

The microcapsule composition of this invention is prepared by (a) providing a microcapsule slurry having a plurality of microcapsules each containing a polymeric wall and an active material encapsulated within the polymeric wall; and (b) curing the microcapsules and coating each of the microcapsules with a deposition protein. In some embodiments, the microcapsules are coated before, during and/or after curing the capsules. Cure and/or coating temperatures can be in the range of 0 to 250° C., 20 to 120° C. or 35 to 75° C. In embodiments where the deposition protein is a protein-silanol copolymer, a protein-silane copolymer, a protein-siloxane copolymer, or a combination thereof, it is preferable that the microcapsules are coated at a temperature between 35 to 75° C. before, during or after curing the microcapsules.

Higher performance of the microcapsules can be achieved by curing at a higher temperature for a longer time. Therefore, in some embodiments, the cross-linked network of polymers containing active materials may be cured for periods of up to 1 hour and more preferably longer than two hours. More preferably, the curing period of the capsule is at least up to about 2 hours, at least up to 3 hours or at least up to 4 hours.

In some embodiments, greater performance of the microcapsules can be achieved when the heating profile to the target cure temperature of the cross-linked network of polymers containing the active material is preferably linear with a heating rate at least up to about 2.0° C. a minute, more preferably at least up to about 5.0° C. a minute, even more preferably at least up to about 8.0° C. a minute and most preferably at least up to about 10° C. a minute over a period of time less than about sixty minutes and more preferably less than thirty minutes. The following heating methods may be used in the practice of the present invention, conduction for example via oil, steam radiation via infrared, and microwave, convection via heated air, steam injection and other methods known by those skilled in the art.

In certain embodiments, the deposition protein is cross-linked on the surface of the microcapsules. In embodiments pertaining to cationically modified deposition proteins, the deposition protein can be cross-linked using a transglutaminase (EC 2.3.2.13), an enzyme capable of catalyzing acyl transfer reactions introducing covalent cross-links between proteins as well as proteins and peptides and primary amines. Transglutaminase can be obtained from several plant, animal or microbial sources. See, e.g., Zhu, et al. (1995) Appl. Microbiol. Biolechnol. 44:277-282 and EP 1068301. Alternatively, a conventional protein cross-linking agent such as glutaraldehyde can be used. As a further alternative, genipin (Methyl (1R,2R,6S)-2-hydroxy-9-(hydroxymethyl)-3-oxabicyclo[4.3.0]nona-4,8-diene-5-carboxylate), an aglycone derived from an iridoid glycoside called geniposide present in fruit of Gardenia jasminoides, has been used to cross-link molecules containing free amino groups in proteins such as fibrin. See, e.g., US 2013/0345321. In particular embodiments, a transglutamase is used to cross-link cationically modified deposition proteins.

In embodiments pertaining to protein-silicon copolymers, the deposition protein can be cross-linked by adding an alkoxysilane. Suitable alkoxysilane cross-linking agents can have the structure $R^1{}_x Si(OR^2)_{4-x}$, wherein x is 0 or 1; and $R^1$ is an optionally substituted $C_1$-$C_8$ alkyl, $C_6$-$C_{14}$ aryl or $C_2$-$C_8$ alkenyl group; and $R^2$ is an optionally substituted linear or branched $C_1$-$C_8$ alkyl, or $C_2$-$C_8$ alkoxyalkyl group, wherein $R^1$ and $R^2$ can be the same or different within the molecule. Exemplary alkoxysilanes are tetraethoxysilane, tetra-n-propoxysilane, methyltriethoxysilane, methyltrimethoxysilane, methyl tri(2-methoxyethoxy)silane, vinyl trimethoxysilane or vinyltriethoxysilane.

Once prepared, the microcapsule composition can be a slurry in a solvent (e.g., water), wherein the microcapsule are at a level of 0.1 to 80% (preferably 1 to 65% and more preferably 5 to 45%) by weight of the microcapsule composition.

In some embodiments, the microcapsule composition is subsequently purified. Purification can be achieved by washing the capsule slurry with water, e.g., deionized or double deionized water, until a neutral pH is achieved. For the purposes of the present invention, the microcapsule suspension can be washed using any conventional method including the use of a separatory funnel, filter paper, centrifugation and the like. The microcapsule suspension can be washed one, two, three, four, five, six, or more times until a neutral pH, e.g., pH 6-8 and 6.5-7.5, is achieved. The pH of the purified microcapsule can be determined using any conventional method including, but not limited to pH paper, pH indicators, or a pH meter.

A microcapsule composition of this invention is "purified" in that it is 80%, 90%, 95%, 97%, 98% or 99% homogeneous to microcapsules. In accordance with the present invention, purity is achieved by washing the microcapsules until a neutral pH is achieved, which is indicative of removal of unwanted impurities and/or starting materials, e.g., polyisocyanate, cross-linking agent and the like.

In certain embodiments of this invention, the purification of the microcapsules includes the additional step of adding a salt to the microcapsules prior to the step of washing the microcapsule suspension with water. Exemplary salts of use in this step of the invention include, but are not limited to, sodium chloride, potassium chloride or bi-sulphite salts. See US 2014/0017287.

Applications. The microcapsule composition of this invention can be formulated for use in consumer products, in particular rinse-off consumer product applications such as shampoo, hair conditioner, body wash, detergent, softener, bar soap, scent booster, or hard surface cleaner. The microcapsule composition can also contain one or more other microcapsule compositions such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof. The microcapsule composition can also contain one or more (e.g., two, three, four, five or six more) different capsules including different capsules of this invention and other capsules such as such as aminoplasts, hydrogel, sol-gel, coascervate capsules, polyurea/polyurethane capsules, and melamine formaldehyde capsules. Further, the microcapsule composition can be combined with free active material.

The microcapsule composition of the present invention are well-suited for use, without limitation, in one or more of the following products:

Household products such as liquid or powder laundry detergents including those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818.

Unit dose pouches, tablets and capsules such as those described in EP 1431382, US 2013/0219996, US 2013/0284637, and U.S. Pat. No. 6,492,315. These unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%). They can contain no water to limit the water content as low as less than 30% (e.g., less than 20%, less than 10%, and less than 5%).

Scent boosters such as those described in U.S. Pat. Nos. 7,867,968, 7,871,976, 8,333,289, US 2007/0269651, and US 2014/0107010.

Fabric care products such as rinse conditioners (containing 1 to 30 weight % of a fabric conditioning active), fabric liquid conditioners (containing 1 to 30 weight % of a fabric conditioning active), tumble drier sheets, fabric refreshers, fabric refresher sprays, ironing liquids, and fabric softener systems such as those described in U.S. Pat. Nos. 6,335,315, 5,674,832, 5,759,990, 5,877,145, 5,574,179, 5,562,849, 5,545,350, 5,545,340, 5,411,671, 5,403,499, 5,288,417, 4,767,547 and 4,424,134

Liquid fabric softeners/fresheners contain at least one fabric softening agent present, preferably at a concentration of 1 to 30% (e.g., 4 to 20%, 4 to 10%, and 8 to 15%). The ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01 to 2.5%, preferably 0.02 to 1.25% and more preferably 0.1 to 0.63%. As another example, when the fabric softening agent is 20% by weight of the fabric softener, the active material is 0.04 to 10%, preferably 0.08 to 5% and more preferably 0.4 to 2.5%. The active material is a fragrance, malodor counteractant or mixture thereof. The liquid fabric softener can have 0.15 to 15% of capsules (e.g., 0.5 to 10%, 0.7 to 5%, and 1 to 3%). When including capsules at these levels, the neat oil equivalent (NOE) in the softener is 0.05 to 5% (e.g., 0.15 to 3.2%, 0.25 to 2%, and 0.3 to 1%).

Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as REWOQUAT WE 18 commercially available from Evonik Industries and STEPANTEX SP-90 commercially available from Stepan Company.

Liquid dish detergents such as those described in U.S. Pat. Nos. 6,069,122 and 5,990,065. Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

All-purpose cleaners including bucket dilutable cleaners and toilet cleaners, bathroom cleaners, bath tissue, rug deodorizers, candles, room deodorizers, floor cleaners, disinfectants, window cleaners, garbage bags/trash can liners, moisture absorbers, household devices such as paper towels and disposable wipes and moth balls/traps/cakes Air Fresheners including room deodorizer and car deodorizer, scented candles, sprays, scented oil air freshener, Automatic spray air freshener, and neutralizing gel beads.

Baby care products such as diaper rash cream/balm, baby powder, and baby care devices such as diapers, bibs and wipes.

Oral care products. Tooth care products (as an example of preparations according to the invention used for oral care) generally include an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or LAPONITE, sweeteners, for example saccharin, taste correctors for unpleasant taste sensations, taste correctors for further, normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol derivatives, (for example L-menthyllactate, L-menthylalkylcarbonates, menthone ketals, menthane carboxylic acid amides), 2,2,2-trialkylacetic acid amides (for example 2,2-diisopropylpropionic acid methyl amide), icilin and icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors.

Tooth Paste. An exemplary formulation includes 40-55% calcium phosphate, 0.8-1.2% carboxymethyl cellulose, 1.5-2.5% sodium lauryl sulfate, 20-30% glycerol, 0.1-0.3% saccharin, 1.0-2.5% flavor oil, water q.s. to 100%. A typical procedure for preparing the formulation includes the steps of (i) mixing by a blender according to the foregoing formulation to provide a toothpaste, and (ii) adding a composition of this invention and blending the resultant mixture till homogeneous.

Other oral care products include, but are not limited to, tooth powders, ral rinses, tooth whiteners, and denture adhesives as well as heath care devices such as dental floss, toothbrushes, and respirators.

Feminine hygiene products such as tampons, feminine napkins and wipes, and pantiliners.

Personal care products including cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a PIT emulsion, a Pickering emulsion, a microemulsion or nano-emulsion; and emulsions which are particularly preferred are of the "oil-in-water" (O/W) type or water-in-oil-in-water (W/O/W) type. More specifically, personal cleansers (bar soaps, body washes, and shower gels), in-shower conditioners, sunscreen and tattoo color protections (sprays, lotions, and sticks), insect repellants, hand sanitizers, antiinflammatory balms, ointments, and sprays, antibacterial ointments and creams, sensates, deodorants and antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deodorant.

An exemplary formulation of a wax-based deodorant includes 10-20% paraffin wax, 5-10% hydrocarbon wax, 10-15% white petrolatum, 2-4% acetylated lanolin alcohol, 4-8% diisopropyl adipate, 40-60% mineral oil, and preservative (as needed). The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.

An exemplary formulation of a Glycol/Soap Type Deodorant includes 60-70% Propylene Glycol, 5-10% Sodium Stearate, 20-30% Distilled Water, and 0.01-0.5% 2,4,4-Trichloro-2'-Hydroxy Diphenyl Ether, manufactured by the Ciba-Geigy Chemical Company and a Trademark of the Ciba-Geigy Chemical Company). The ingredients are combined and heated to 75° C. with stirring until the sodium stearate has dissolved. The resulting mixture is cooled to 40° C. followed by addition of a composition of this invention.

Other personal care products include lotions (e.g., body lotion, facial lotion, and hand lotion, body powder and foot powder, toiletries, body spray, shave cream and male grooming products, bath soak, and exfoliating scrub as well as personal care devices such as facial tissues and cleansing wipes.

Hair care products include, but are not limited to, shampoos (liquid and dry powder), hair conditioners (rinse-out conditioners, leave-in conditioners, and cleansing conditioners), hair rinses, hair refreshers, hair perfumes, hair straightening products, hair styling products, hair fixative and styling aids, hair combing creams, hair wax, hair foam, hair gel, nonaerosol pump spray, hair bleaches, hair dyes, hair colorants, perming agents, and hair wipes.

Beauty care products include, but are not limited to, fine Fragrances, solid perfumes, lipstick/lip balm, make-up cleanser, skin care cosmetics such as foundation, pack, sunscreen, skin lotion, milky lotion, skin cream, emollients, skin whitening and make-up cosmetics including manicure, mascara, eyeliner, eye shadow, liquid foundation, powder foundation, lipstick and cheek rouge.

Compositions and methods for incorporating fragrance capsules into alcoholic fine fragrances are described in U.S. Pat. No. 4,428,869. Alcoholic fine fragrances may contain the following 1-99% Ethanol, 0-99% water, 0.1-1% suspending aide including, but not limited to, hydroxypropyl cellulose, ethyl cellulose, silica, microcrystalline cellulose, carrageenan, propylene glycol alginate, methyl cellulose, sodium carboxymethyl cellulose or xanthan gum, and an optional emulsifier or emollient.

Consumer goods packaging such as fragranced cartons, fragranced plastic bottles/boxes are also encompassed within the scope of this invention as are pet care products such as cat litter, Flea and tick treatment products, Pet grooming products, pet shampoos, pet toys, pet treats, pet chewables, pet training pags and pet carriers and crates.

The above-listed applications are all well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547, and 4,424,134. Liquid laundry detergents include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Liquid dish detergents are described in U.S. Pat. Nos. 6,069,122 and 5,990,065. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Automatic Dish Detergents are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The invention is described in greater detail by the following non-limiting examples. Without further elaboration, it is believed that one skilled in the art can, based on the description herein, utilize the present invention to its fullest extent.

Example 1: Discovery of VOLUMINIS (Protein Modified with Cationic Group) as Efficient Deposition Aid COMPOSITION 1: Polyurea capsule+VOLUMINIS. 192.0 g of a fragrance Apple (International Flavors and Fragrance Inc., Union Beach, N.J.) was weighed out and combined with 48.0 g of caprylic/capric triglyceride (NEOBEE), and 19.2 g of polymethylene polyphenylpolyisocyanate (LUPRANATE), to form the oil phase. In a separate beaker, 3 g of naphthalene sulfonate condensate (MORWET D-425) was dissolved in 316.2 g distilled water to make the aqueous solution. This was then emulsified with the previously prepared oil phase to form the fragrance emulsion under high shearing (IKA—ULTRA TURRAX, T25 Basic) at 9500 rpm for three minutes. The fragrance emulsion was heated to a 35° C. and 21.6 g of 40.0% hexamethylene diamine was added under constant mixing with an overhead mixer. After 15 minutes of stirring at 35° C., the capsule slurry was cured at 55° C. for two hours. After two hours, the capsule slurry was allowed to cool back down to room temperature under constant mixing.

Freshly prepared capsule slurry (83.8 g) was then mixed with 3.8 g of VOLUMINIS-LQ-WD (Croda, Table 3) using an overhead mixer for 30 minutes at room temperature.

COMPARISON 1: Polyurea Caspule+CRODASONE. This comparative capsule was prepared following the same procedure as Composition 1 except, 82.9 g of freshly prepared capsule slurry was mixed with 2.9 g of CRODASONE W-LQ-(WD) (Croda, Table 3) using an overhead mixer for 30 minutes at room temperature.

COMPARISON 2: Polyurea Capsule+KERAVIS. This comparative capsule was prepared following the same procedure as Composition 1 except, 84.0 g of freshly prepared capsule slurry was mixed with 4.0 g of KERAVIS-LQ-(WD) (Croda, Table 3) using an overhead mixer for 30 minutes at room temperature.

TABLE 3

| | Molecular Weight | Description |
|---|---|---|
| VOLUMINIS | 50000 | Ethyltrimmoniumchloride methacrylate-wheat protein copolymer |
| CRODASONE | 50000 | Hydrolyzed wheat protein PG-propyl silantriol |
| KERAVIS | 1800 | Hydrolyzed vegetable protein PG-propyl silantriol |

Fragrance Intensity in Shampoo. The performance of Composition 1 and Comparisons 1-2 was evaluated in shampoo. More specifically, each composition was blended into a model shampoo (MAGICK Botanical). To the shampoo base was added 0.5% fragrance oil equivalent of the capsule slurries. The base was subsequently mixed at high shear, 4000-6000 rpm for 1-2 minutes. To two bundle hair swatches (8 strands) that were wetted under water, with excess water squeezed lightly, was added 2.0 g of the prepared hair shampoo base. After the hair was lathered, the hair swatches were rinsed under a stream of water (38° C., 1 gal/min) for 45 seconds, excess water from hair was removed. Hair swatches were line-dried for 24 hours followed by sensory evaluation by a panel of judges. The fragrance intensity was rated on a scale ranging from 0 to 10 pre- and post-brushing the hair swatches with a typical comb. A numerical value of 5 indicated the hair swatches produced a strong intensity, while a value of 10 indicated the hair swatches generated a very strong smell. The results are summarized in Table 4.

TABLE 4

| | Shampoo Performance (Intensity) | |
|---|---|---|
| Composition | Pre-brush | Post-brush |
| 1 | 1.4 | 4.4 |
| Comparison 1 | 0.50 | 1.3 |
| Comparison 2 | 1.1 | 1.6 |

It was surprisingly found that Composition 1 showed significant post-brush benefits from shampoo. Based on knowledge of cationic-base materials, performance has never been found at such a low molecular weight range. Furthermore, performance was only observed when cationic property was combined with the protein.

Fragrance Intensity in a Liquid Detergent Base. The performance of Composition 1 and Comparisons 1-2 was also evaluated in a liquid detergent base. More specifically, Composition 1 and Comparisons 1-2 were each blended into a model un-fragrance liquid detergent base at 0.5% fragrance oil equivalence. The resulting base was applied to a standard US washing machine protocol with towels as described in U.S. Pat. No. 8,299,011. The towels were line-dried for 24 hours followed by sensory evaluations by a panel of judges. The fragrance intensity was rated on a scale ranging from 0 to 35 at pre- and post-rubbing the towel swatches. A numerical value of 15 indicated the towel producing a strong intensity, while 35 indicated the towel generated a very strong smell. The results are summarized in Table 5.

TABLE 5

| | Liquid Detergent (Intensity) | |
|---|---|---|
| Composition | Pre-rub | Post-rub |
| 1 | 4.8 | 10.8 |
| Comparison 1 | 2.6 | 4.2 |
| Comparison 2 | 2.7 | 4.0 |

It was surprisingly found that Composition 1 showed significant post-rub benefit from liquid detergent. Again, this was the first time to observe such a high performance with low molecular weight cationic polymer. Further, performance was only observed when cationic moiety was present with the protein.

Example 2: Discovery of Efficient Use of CRODASONE (Protein Modified with Silanetriol Group) as Deposition System when Post-Polymerized Via Heat Treatment with Additional Deposition Aid COMPOSITION 2: Polyurea Capsule+CRODASONE+Deposition Polymers+Heat. 192.0 g of a fragrance Apple (International Flavors and Fragrance Inc., Union Beach, N.J.) was weighed out and combined with 48.0 g of caprylic/capric triglyceride (NEOBEE), and 19.2 g of polymethylene polyphenylpolyisocyanate (LUPRANATE), to form the oil phase. In a separate beaker, 3 g of naphthalene sulfonate condensate (MORWET D-425) was dissolved in 244.3 g distilled water to make the aqueous solution. This was then emulsified with the previously prepared oil phase to form the fragrance emulsion under high shearing (IKA—ULTRA TURRAX, T25 Basic) at 9500 rpm for three minutes. The fragrance emulsion was heated to 35° C. and 21.6 g of 40.0% hexamethylene diamine was added under constant mixing with an overhead mixer. After 15 minutes of stirring at 35° C., 20.8 g of CRODASONE W-LQ-(WD) (Croda) was added and the capsule slurry was heated to 55° C., at which point 28.6 g of LUPAMIN 9095 (BASF) was added. After one hour of curing, 22.5 g of MERQUAT 100 (Lubrizol) was added and cured for additional 1 hour at 55° C., at which time the capsule slurry was allowed to cool back down to room temperature under constant mixing.

COMPARISON 3: Polyurea Capsule+CRODASONE+Deposition Polymers+No Heat. To 0.81 g of COMPARISON 2 was mixed with 0.04 g of LUPAMIN followed by 0.03 g of MERQUAT 100 (Luprizol) at room temperature and mixed with a spatula until a homogenous mixture was obtained.

COMPARISON 4: Polyurea Capsule+KERAVIS+Deposition Polymers+Heat. This comparative capsule was prepared following the same procedure as Composition 1 except, 236.4 g of distilled water and 28.7 g of KERAVIS-LQ-(WD) (Croda) was added.

COMPARISON 5: Polyurea Capsule+KERAVIS Deposition Polymers+No Heat. To 0.82 g of COMPARISON 3 was mixed with 0.04 g of LUPAMIN followed by 0.03 g of MERQUAT 100 (Luprizol) at room temperature using a spatula until a homogenous mixture was obtained.

Fragrance Intensity in Shampoo. The performance of Composition 2 and Comparisons 3-5 was evaluated in shampoo. More specifically, Composition 2 and Comparisons 3-5 were each blended into a model shampoo (MAGICK Botanical). To the shampoo base was added 0.5% fragrance oil equivalent of the capsule slurries. The slurry was mixed at high shear, 4000-6000 rpm for 1-2 minutes. To two bundle hair swatches (8 strands) that were wetted under water, with excess water squeezed lightly, was added 2.0 g of the prepared hair shampoo base. After the hair was lathered, the hair swatches were rinsed under a stream of water (38° C., 1 gal/min) for 45 seconds, excess water from hair was removed. Hair swatches were line-dried for 24 hours followed by sensory evaluation by a panel of judges. The fragrance intensity was rated on a scale ranging from 0 to 10 pre- and post-brushing the hair swatches with a typical comb. A numerical value of 5 indicated the hair swatches produced a strong intensity, while a value of 10 indicated the hair swatches generated a very strong smell. The results are summarized in Table 6.

TABLE 6

| Composition | Shampoo Performance (Intensity) | |
|---|---|---|
| | Pre-brush | Post-brush |
| 2 | 1.4 | 3.6 |
| Comparison 3 | 0.7 | 0.9 |
| Comparison 4 | 0.7 | 1.3 |
| Comparison 5 | 0.5 | 0.9 |

It was surprisingly found that Composition 2 showed significant post-brush benefits from shampoo, when heating was used to induce post-polymerization of the silane-triol group found in CRODASONE. It was also found that while a similar silane-triol group was present in KERAVIS, heat-induced post-polymerization did not help with increasing the performance significantly. This may be attributed to the much lower molecular weight of KERAVIS compared to CRODASONE. A higher concentration of KERAVIS may increase the performance.

Example 3: Discovery of CRODASONE (Protein Modified with Silanetriol Group) Heat Treatment with Additional Deposition Aid Showing Efficiency Against Neutral Charged Capsules COMPOSITION 3: Neutral Polyurea Capsule+CRODASONE+Deposition Polymers+Heat. This composition was prepared following the same procedure as Composition 2 except, 3 g of partially hydrolyzed polyvinyl alcohol (MOWIOL 3-83-Kuraray) was used.

COMPARISON 6: Neutral Polyurea Capsule+CRODASONE+Deposition Polymer+No Heat. This comparative capsule was prepared following the same procedure as Comparison 2 except 3 g of partially hydrolyzed polyvinyl alcohol (MOWIOL 3-83-Kuraray) was used. Then to 0.81 g of freshly prepared slurry was mixed with 0.04 g of LUPAMIN followed by 0.03 g of MERQUAT 100 (Luprizol) at room temperature and using a spatula until homogenous mixture was obtained.

COMPARISON 7: Neutral Polyurea Capsule+KERAVIS+Deposition Polymer+Heat. This comparative capsule was prepared following the same procedure as COMPARISON 4 except, 3 g of partially hydrolyzed polyvinyl alcohol (MOWIOL 3-83-Kuraray) was used.

COMPARISON 8: Neutral Polyurea Capsule+KERAVIS+Deposition Polymer+No Heat. This comparative capsule was prepared following the same procedure as Comparison 3 except, 3 g of partially hydrolyzed polyvinyl alcohol (MOWIOL 3-83-Kuraray) was used. Then to 0.82 g of freshly prepared slurry was mixed with 0.04 g of LUPAMIN followed by 0.03 g of MERQUAT 100 (Luprizol) at room temperature and using a spatula until homogenous mixture was obtained.

COMPARISON 9: Neutral Polyurea Capsule+VOLUMINIS+No Heat. This comparative capsule was prepared following the same procedure as Composition 1 except, 3 g of partially hydrolyzed polyvinyl alcohol (MOWIOL 3-83-Kuraray) was used.

COMPARISON 10: Neutral Polyurea Capsule+VOLUMINIS+Deposition Polymer+No Heat. To 0.82 g of Comparative 9 was mixed with 0.04 g of LUPAMIN followed by 0.03 g of MERQUAT 100 (Luprizol) at room temperature using a spatula until homogenous mixture was obtained.

COMPARISON 11: Polyurea Capsule. This comparative capsule was prepared following the same procedure as Composition 1 except, no VOLUMINIS-LQ-WD (Croda) was added.

COMPARISON 12: Neutral Polyurea Capsule. This comparative capsule was prepared following the same procedure as Comparison 9 except, no VOLUMINIS-LQ-WD (Croda) was added.

Fragrance Intensity in Shampoo. The performance of Composition 3 and Comparisons 6-10 was evaluated in shampoo. More specifically Composition 3 and Comparisons 6-10 were each blended into a model shampoo (MAGICK Botanical). To the shampoo base was added 0.5% fragrance oil equivalent of the capsule slurries. The slurries were mixed at high shear, 4000-6000 rpm for 1-2 minutes.

To two bundle hair swatches (8 strands) that were wetted under water, with excess water squeezed lightly, was added 2.0 g of the prepared hair shampoo base. After the hair was lathered, the hair swatches were rinsed under a stream of water (38° C., 1 gal/min) for 45 seconds, excess water from hair was removed. Hair swatches were line-dried for 24 hours followed by sensory evaluation by a panel of judges. The fragrance intensity was rated on a scale ranging from 0 to 10 pre- and post-brushing the hair swatches with a typical comb. A numerical value of 5 indicated the hair swatches produced a strong intensity, while a value of 10 indicated the hair swatches generated a very strong smell. The results are summarized in Table 7.

TABLE 7

| Composition | Shampoo Performance (Intensity) | |
| --- | --- | --- |
| | Pre-brush | Post-brush |
| 3 | 1.7 | 3.9 |
| Comparison 6 | 0.3 | 0.5 |
| Comparison 7 | 0.8 | 2.1 |
| Comparison 8 | 0.6 | 1.2 |
| Comparison 9 | 0.5 | 0.9 |
| Comparison 10 | 0.3 | 0.6 |

It was surprisingly found that Composition 3 showed significant post-brush benefits from shampoo, when heating was used to induce the post-polymerization process of the silane-triol group found in CRODASONE, while the capsule charged was more neutral. As indicated in Table 8, capsule with MORWET D-425 as a dispersant had a higher negative surface charge. Whereas when the dispersant was replaced with MOWIOL 3-83, the capsule was more neutral. With more negative charge, better interaction was usually observed with cationic materials therefore better performance. The post-polymerization step of CRODASONE may have increased the interaction process of the cationic material to the more neutral surface. While some benefits were observed using KERAVIS, the fragrance intensity was not as high. This again may be attributed to the much lower molecular weight of KERAVIS compared to CRODASONE. Thus, a higher concentration of KERAVIS may increase the performance.

TABLE 8

| | Dispersant | Capsule Surface Charge (mV) |
| --- | --- | --- |
| Comparison 11 | MORWET D-425 | −56.6 |
| Comparison 12 | MOWIOL 3-83 | −6.3 |

What is claimed is:

1. A microcapsule composition comprising a plurality of microcapsules each containing a polymeric wall and an active material encapsulated within the polymeric wall, wherein the active material contains a fragrance, a profragrance, or both; the polymeric wall contains a milk protein, vegetable protein or gelatin and 0.2% to 5% trimethylol propane-adduct of xylylene diisocyanate, based on the weight of the microcapsule composition; and wherein the microcapsule composition further comprises modified starch, xanthan, Arabic gum, or a combination thereof.

2. The microcapsule composition of claim 1, wherein the vegetable protein is a potato protein.

3. The microcapsule composition of claim 1, further comprising guanidine carbonate.

4. A consumer product comprising a consumer product base and a microcapsule composition of claim 1.

5. The consumer product of claim 1, wherein the consumer product is a fabric conditioner, detergent, fabric spray, personal wash product, home care product, liquid soap, shampoo, rinse-off conditioner, or leave-on conditioner.

* * * * *